United States Patent
Slater et al.

(10) Patent No.: US 8,439,593 B2
(45) Date of Patent: May 14, 2013

(54) QUARTER TURN LOCKING MECHANISM

(75) Inventors: Nicholas Slater, Chandler, AZ (US);
Joshua A. Butters, Chandler, AZ (US);
Carlyle J. Creger, Wellsville, UT (US)

(73) Assignee: IMDS Corporation, Logan, UT (US)

( * ) Notice: Subject to any disclaimer, the term of this patent is extended or adjusted under 35 U.S.C. 154(b) by 214 days.

(21) Appl. No.: 12/943,586

(22) Filed: Nov. 10, 2010

(65) Prior Publication Data
US 2011/0110716 A1 May 12, 2011

Related U.S. Application Data

(60) Provisional application No. 61/259,722, filed on Nov. 10, 2009.

(51) Int. Cl.
*F16D 1/00* (2006.01)
(52) U.S. Cl.
USPC ............................................ 403/361; 403/348
(58) Field of Classification Search .................... 403/19, 403/348, 349, 361; 606/86 A, 86 B, 99, 104
See application file for complete search history.

(56) References Cited

U.S. PATENT DOCUMENTS

| 796,306 | A | 8/1905 | Exley |
|---|---|---|---|
| 1,885,321 | A | 11/1932 | Benn |
| 4,007,516 | A | 2/1977 | Coules |
| 4,331,413 | A | 5/1982 | Hoen |
| 4,632,433 | A | 12/1986 | Kimura |
| 4,647,262 | A | 3/1987 | Yokota |
| 4,648,635 | A | 3/1987 | Juhling |
| 5,087,086 | A | 2/1992 | Snedeker |
| 5,496,323 | A | 3/1996 | Dye |
| 5,683,399 | A | 11/1997 | Jones |
| 5,875,976 | A | 3/1999 | Nelson |
| 6,095,572 | A | 8/2000 | Ford |
| 6,179,302 | B1 | 1/2001 | Gauthier |
| 6,361,687 | B1 | 3/2002 | Ford |
| D472,797 | S | 4/2003 | Ellis |
| 6,626,913 | B1 | 9/2003 | McKinnon |
| D484,031 | S | 12/2003 | Ellis |
| 6,764,499 | B2 | 7/2004 | Honey |
| 6,808,407 | B1 | 10/2004 | Cannon |
| 6,827,536 | B1 | 12/2004 | Leon |
| 6,986,790 | B2 | 1/2006 | Ball |
| 7,147,399 | B2 * | 12/2006 | Viscount et al. .............. 403/349 |
| 7,182,786 | B2 | 2/2007 | Justin |
| 7,223,291 | B2 | 5/2007 | Errico |
| 7,354,289 | B2 | 4/2008 | Cannon |
| 7,677,418 | B2 | 3/2010 | Henniges |
| 7,922,730 | B2 * | 4/2011 | Raines, Jr. .................... 606/104 |
| 7,947,047 | B2 * | 5/2011 | Arnal ............................ 606/104 |

(Continued)

FOREIGN PATENT DOCUMENTS
WO    WO0051530    9/2000

*Primary Examiner* — Michael P Ferguson
(74) *Attorney, Agent, or Firm* — G. So Hays; James Larson; Barbara Daniels

(57) ABSTRACT

Apparatus and methods are disclosed for securely, yet releasably, connecting separate parts. A shaft engages a cooperating socket to form a connection capable of sustaining service loads. The shaft has a protruding pin which slides within a slot in the socket to guide the shaft into locked engagement with the socket. The shaft also has a cantilever body which wedges into a tapered region in the socket to frictionally bind the shaft and socket together.

20 Claims, 20 Drawing Sheets

U.S. PATENT DOCUMENTS

| | | |
|---|---|---|
| 2003/0036779 A1 | 2/2003 | Westland |
| 2005/0249550 A1* | 11/2005 | Liang .......................... 403/348 |
| 2006/0111715 A1 | 5/2006 | Jackson |
| 2007/0162145 A1 | 7/2007 | Justin |
| 2007/0233153 A1 | 10/2007 | Shipp |
| 2008/0262547 A1 | 10/2008 | Lewis |
| 2008/0269768 A1* | 10/2008 | Schwager et al. ............ 606/104 |
| 2009/0112209 A1* | 4/2009 | Parrott et al. ................. 606/104 |
| 2011/0004255 A1* | 1/2011 | Weiner et al. ................. 606/104 |

* cited by examiner

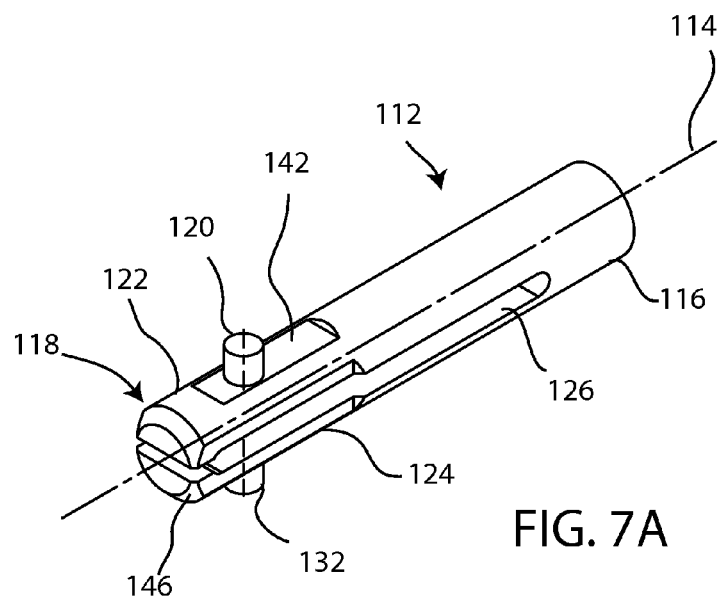
FIG. 7A
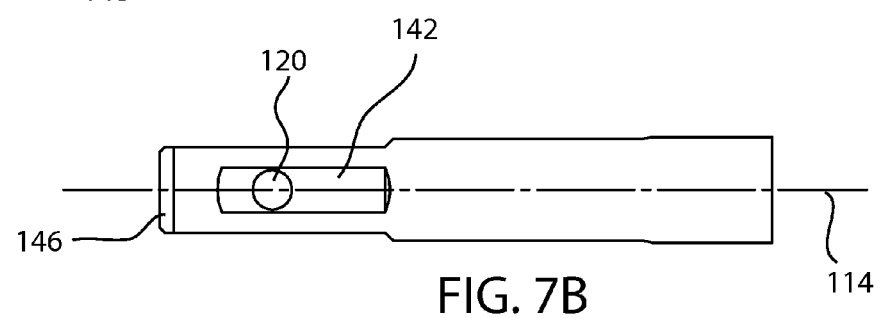
FIG. 7B
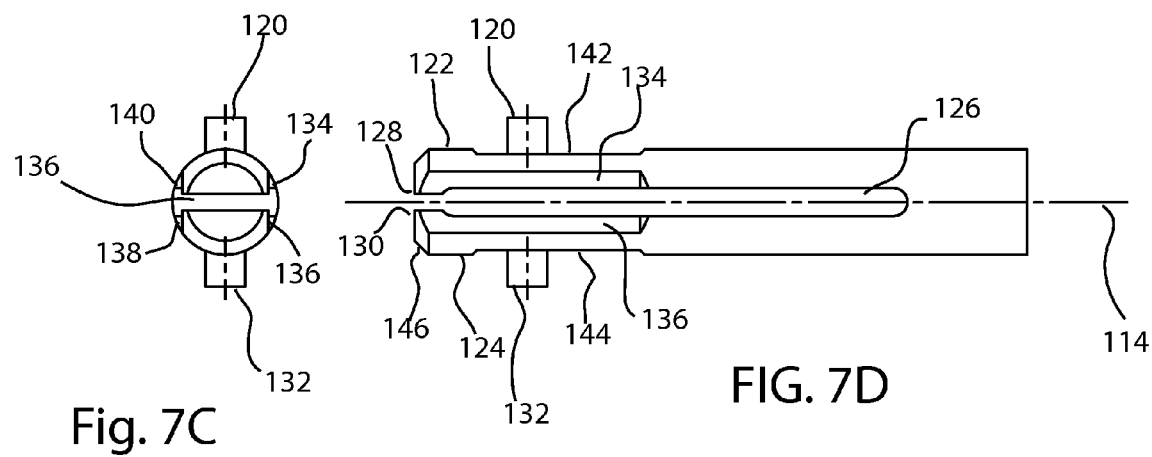
Fig. 7C
FIG. 7D

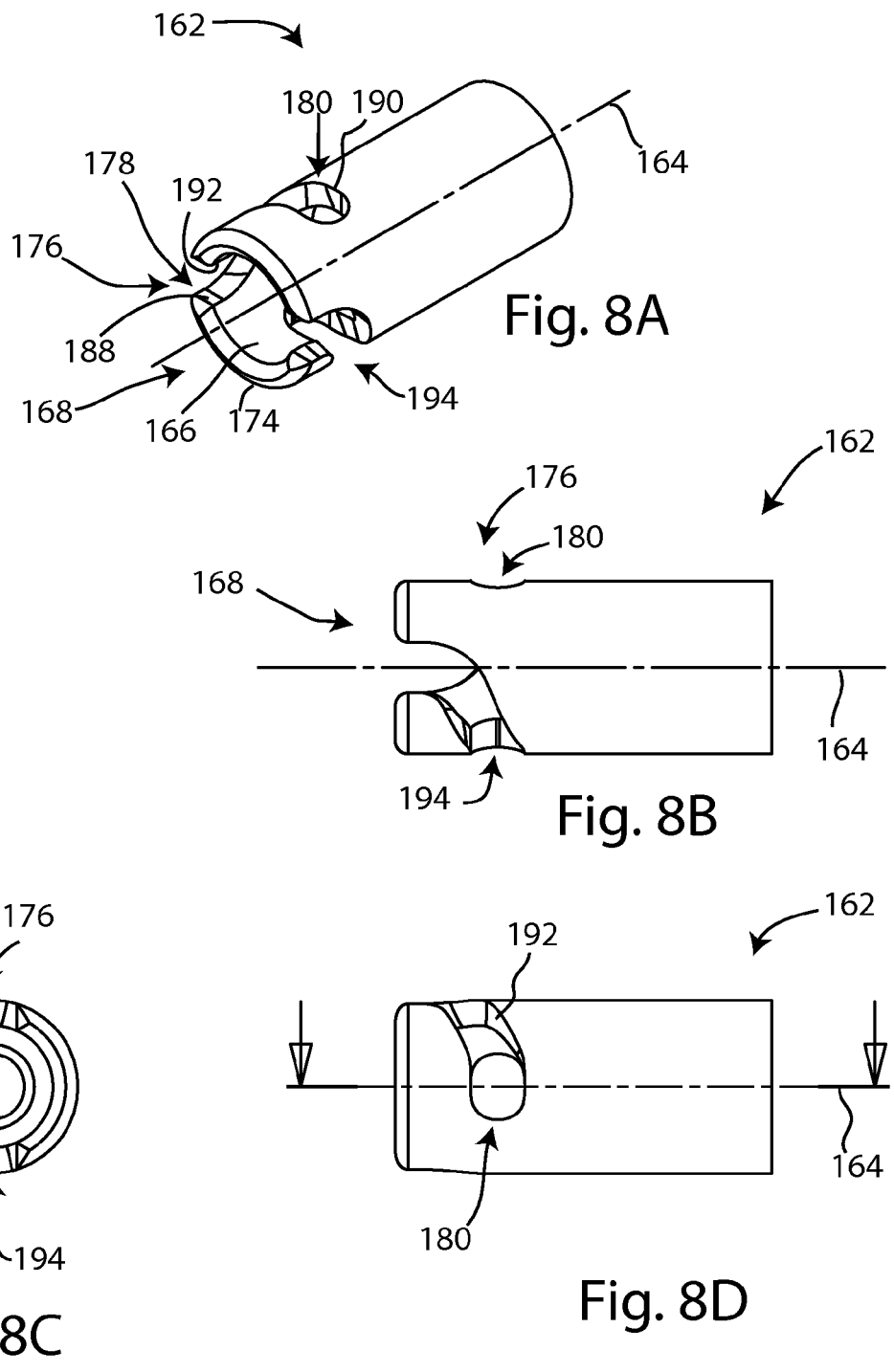

QUARTER TURN LOCKING MECHANISM

CROSS-REFERENCE TO RELATED APPLICATIONS

This application claims the benefit of the filing date of U.S. Application No. 61/259,722, which was filed on Nov. 10, 2009, is entitled QUARTER TURN LOCKING MECHANISM FOR SURGICAL INSTRUMENT CONNECTION. The contents of U.S. Application No. 61/259,722 are hereby incorporated by reference as part of this application.

BACKGROUND OF THE INVENTION

The present disclosure relates to interconnections for securely yet releasably connecting separate components. In certain embodiments, quarter turn locking mechanisms are disclosed. Specific embodiments are disclosed in the context of a spinal system comprising a trial implant and an inserter tool.

SUMMARY OF THE INVENTION

The present disclosure sets forth components, systems, kits, and methods for securely yet releasably connecting separate parts. In an embodiment, a spinal trial implant inserter tool and a spinal trial implant are securely, yet releasably, connected. The connection is capable of sustaining intraoperative loads as the spinal trial implant is maneuvered relative to the spine. The connection may be connected and disconnected quickly and easily when desired. The connection relies upon cooperating features on the tool and the trial. The geometry of the cooperating features is relatively insensitive to dimensional variation, therefore relatively larger manufacturing tolerances may be specified without sacrificing acceptable function.

BRIEF DESCRIPTION OF THE DRAWINGS

FIG. 7A is a perspective view of a shaft; FIG. 7B is a top view of the shaft of FIG. 7A; FIG. 7C is an end view of the shaft of FIG. 7A; and FIG. 7D is a front view of the shaft of FIG. 7A;

FIG. 8A is a top perspective view of a socket; FIG. 8B is a top view of the socket of FIG. 8A; FIG. 8C is an end view of the socket of FIG. 8A; FIG. 8D is a front view of the socket of FIG. 8A.

DETAILED DESCRIPTION

While certain embodiments have been shown and described in detail below, it will be clear to the person skilled in the art upon reading and understanding this disclosure that changes, modifications, and variations may be made and remain within the scope of the components, systems, kits, and methods described herein. Furthermore, while various features are grouped together in the embodiments for the purpose of streamlining the disclosure, it is appreciated that features from different embodiments may be combined in a mix and match fashion.

The following description and accompanying drawings are offered by way of illustration only. In particular, while the present disclosure sets forth an embodiment in the context of surgical instruments, one of skill in the art will appreciate that the components, systems, kits, and methods may be applicable outside the realm of surgical instruments or the field of medicine altogether.

Not every feature of each embodiment is labeled in every figure in which that embodiment appears, in order to keep the figures clear. Similar reference numbers (e.g., those that are identical except for the first numeral) are used to indicate similar features in different embodiments.

Standard medical planes of reference and descriptive terminology are employed in this specification. A sagittal plane divides a body into right and left portions. A mid-sagittal plane divides the body into equal right and left halves. A coronal plane divides a body into anterior and posterior portions. A transverse plane divides a body into superior and inferior portions. Anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body.

Figure 1:
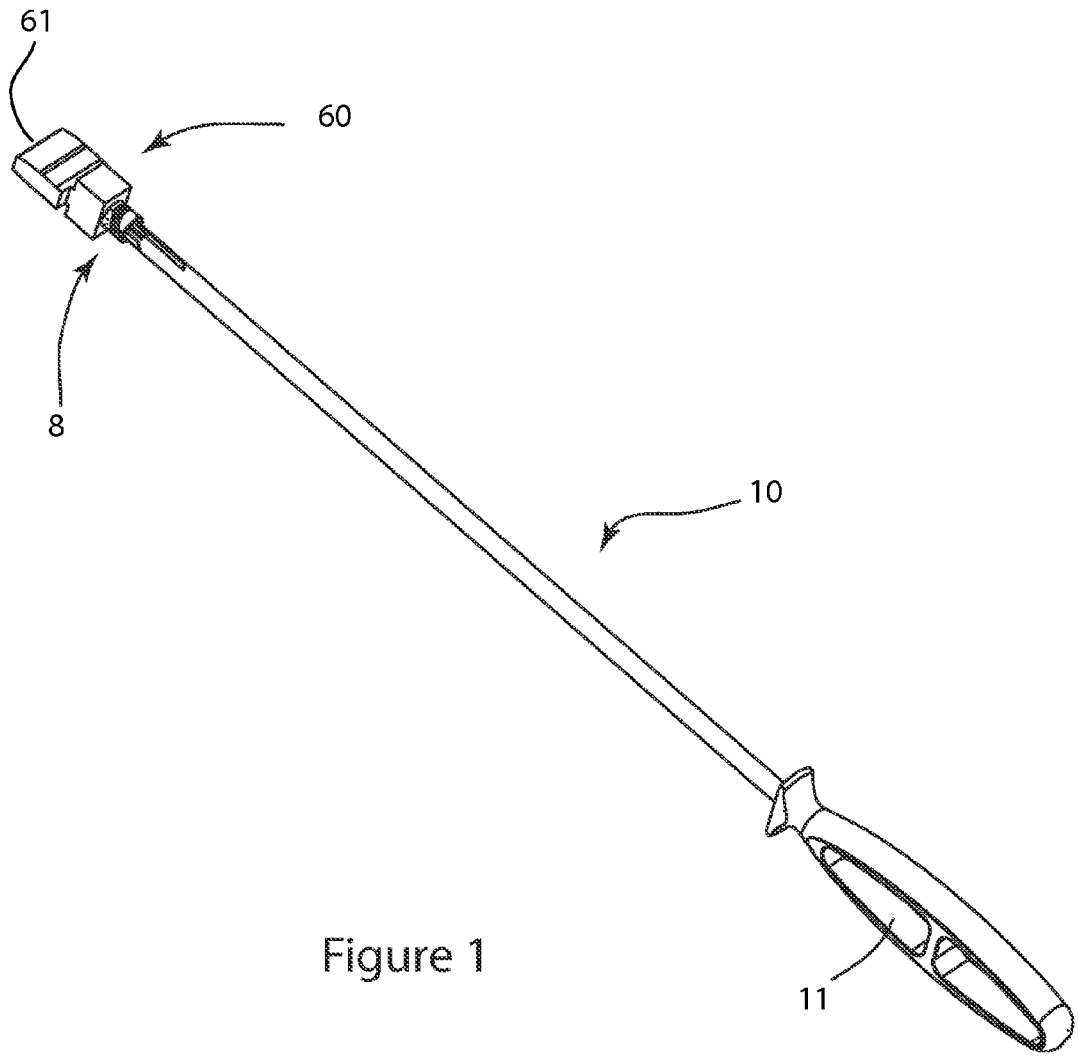
FIG. 1 is a perspective view of a spinal trial implant and an inserter tool.

Referring to FIG. 1, an embodiment of a locking mechanism is shown in the context of a system for spinal surgery. An inserter tool 10 is shown connected to a trial implant 60 by means of a connection mechanism 8. The trial 60 includes a mock implant body portion 61 which may be positioned within an intervertebral disc space in order to determine the proper size for a spinal implant (not shown) for permanent implantation. The tool 10 includes a handle 11. The tool 10 is used to hold and manipulate the trial 60 as the trial 60 is inserted into the intervertebral disc space. The connection mechanism 8 between the trial 60 and the tool 10 may have cooperating features on the trial 60 and the tool 10 which releasably couple the trial 60 and the tool 10. The connection mechanism 8 may be subjected to service loads which are oriented with respect to one or more of three mutually perpendicular axes. The service loads may act along an axis, such as tensile or compressive loads, or around an axis, such as a torque load. Furthermore, service loads may be a combination of axial and/or torque loads along and/or around any or all of the three mutually perpendicular axes. The three mutually perpendicular axes may be aligned with respect to the structure of the trial 60 and/or the tool 10 or with respect to anatomic planes and/or axes of reference.

Figure 2:
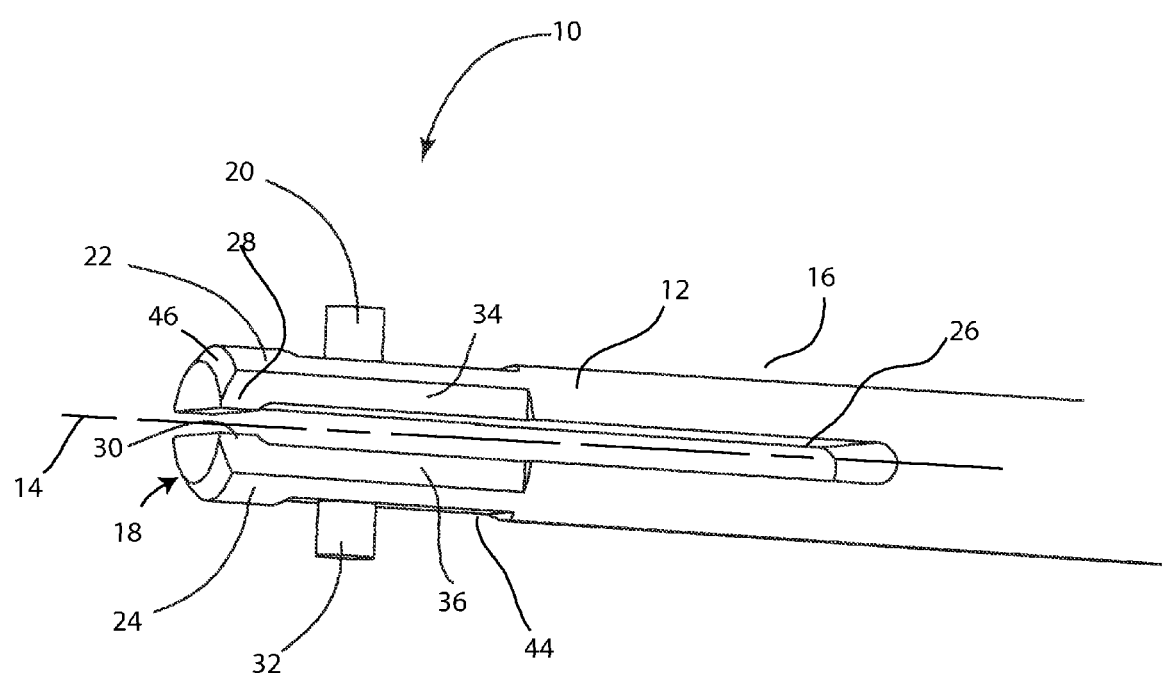
FIG. 2 is a perspective detail view of a distal end of the inserter tool of FIG. 1.

Referring to FIG. 2, the tool 10 may have a shaft 12 with a longitudinal axis 14 centered in the shaft 12. The axis 14 may be described as an axis of revolution or axis of radial symmetry of the basic shaft 12.

The shaft 12 may have an outer diameter 16, a tip end 18, and a first pin 20. The tip end 18 may also be described as a working end of the shaft 12, in the sense that tip end 18 may have features to connect the tool 10 to the trial 60. The first pin 20 may be proximate the tip end 18. The first pin 20 protrudes outwardly beyond the outer diameter 16 of the shaft 12. The first pin 20 may protrude normal to the outer diameter 16 and orthogonal to the axis 14. The first pin 20 may be cylindrical.

The tip end 18 may be split into a plurality of cantilever bodies 22, 24. The cantilever bodies 22, 24 are so named because they function as cantilever flex beams, as will be described presently in more detail. The cantilever bodies 22, 24 may also be described as resilient prongs which extend alongside axis 14. The tip end 18 may be split into two cantilever bodies 22, 24 by slit 26. Slit 26 may also be described as a slot or notch.

Slit 26 is shown extending through the tip end 18 and along a portion of the shaft 12. Slit 26 may extend completely across the shaft 12 in a direction orthogonal to the first pin 20. Slit 26 may have a uniform width over most of its length. In other words, slit 26 may provide a uniform separation, or gap, between cantilever bodies 22, 24 over most of their length. For a given material, the width of slit 26 may be designed so that cantilever bodies 22, 24 provide a desired resistance to pinching the slit 26 closed at the tip end 18. The width of slit 26 may also step down, or become narrower, proximate the tip end 18, so as to form opposing raised bosses 28, 30 between the cantilever bodies 22, 24 at the tip end 18. The bosses 28, 30 may serve to protect the shaft 12 from overload conditions during use. More specifically, for a given material, the width of slit 26 at the tip end 18 between the bosses 28, 30 may be selected so that the shaft 12 experiences only elastic deformation, even when slit 26 is squeezed completely closed at the tip end 18 so that the bosses 28, 30 touch. In other words, stresses in shaft 12 remain below an elastic limit of the shaft 12 material because bosses 28, 30 serve as physical stops to prevent excess deflection of the cantilever bodies 22, 24.

The first pin 20 may be situated on a first cantilever body 22. Shaft 12 may include a second pin 32 like the first pin 20. The second pin 32 may be in a position that is rotated around the axis 14 relative to the first pin 20, so that the first pin 20 and the second pin 32 are arranged in a circular array around the axis 14. In FIG. 2, the second pin 32 is in a position that is rotated 180 degrees from the first pin 20, so that the pins 20, 32 are symmetrically arranged around the axis 14 on opposite sides of the shaft 12.

Figure 4:
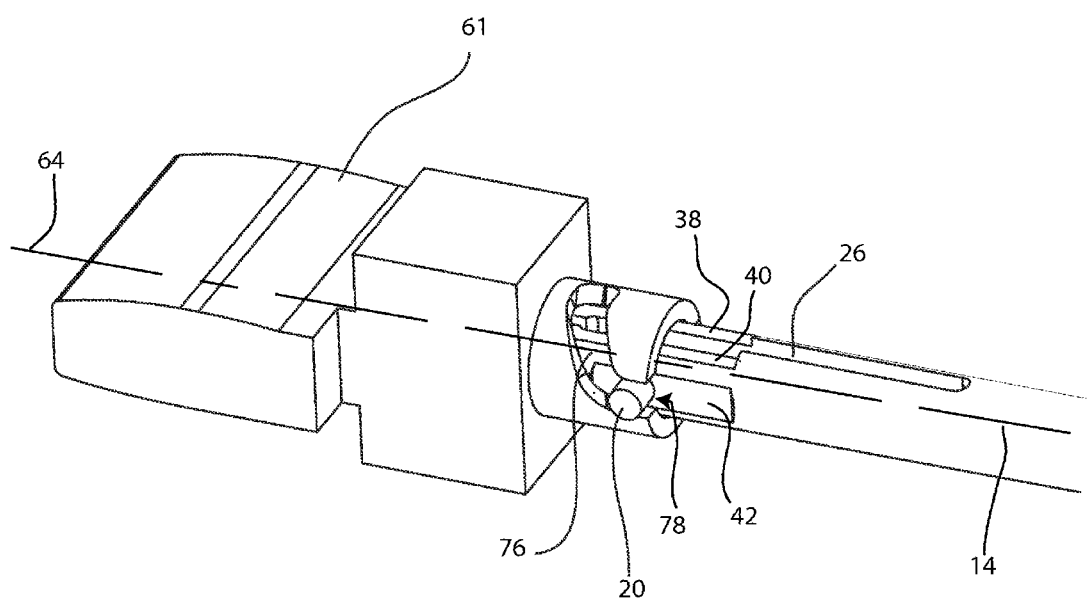
FIG. 4 is a perspective view of the spinal trial implant and inserter tool of FIG. 1, with the inserter tool partially inserted into the trial.

The shaft 12 may have flattened portions 34, 36, 38, 40 along the outer diameter 16 where the slit 26 breaks through the shaft 12, as illustrated in FIGS. 2 and 4. The flattened portions 34, 36, 38, 40 soften, or break, edges along the intersection of slit 26 and outer diameter 16. The flattened portions 34, 36, 38, 40 also make the cantilever bodies 22, 24 narrower.

The shaft 12 may have flattened regions 42, 44 around the first and second pins 20, 32, as illustrated in FIGS. 2 and 4.

The tip end 18 of shaft 12 may have a circumferentially bevel 46. The bevel 46 softens, or breaks, an edge where the outer diameter 16 terminates at the tip end 18. The bevel 46 also tapers the tip end 18.

The shaft 12 may be fabricated from polymers, metals, ceramics, composites, glass, wood, or other materials according to the requirements of a particular application. The shaft 12 may be fabricated from a combination of materials, so that each feature of the shaft 12 is fabricated from a material suitable to the particular requirements of the individual feature. In the context of surgical instruments, implants, and systems, it is contemplated that the shaft 12 may be fabricated from polymers such as polyetheretherketone (PEEK), acetal, or ultra high molecular weight polyethylene (UHMWPE), or from metals comprising iron, chrome, titanium, nickel, or molybdenum.

Referring to FIGS. 3A-C and 6, the trial 60 may have a tube or socket 62 with a longitudinal axis 64 centered in the socket 62. The axis 64 may be described as an axis of revolution or axis of radial symmetry of the basic socket 62.

The socket 62 may have an inner diameter 66, an open end 68, a second end 70, a tapered region 72, a side wall 74, and a first slot 76. The inner diameter 66 extends between the open end 68 and the tapered region 72. The second end 70 is opposite the open end 68, thus in this embodiment, the second end 70 is deep within the socket 62. The second end 70 may be closed, or blind. The tapered region 72 is inside the socket 62, between the inner diameter 66 and the second end 70, and distant from the open end 68. The tapered region 72 may be oriented to form a tapered constriction, such that the second end 70 is smaller than the inner diameter 66.

The first slot 76 may project through the side wall 74 of the socket 62.

Figure 3A:
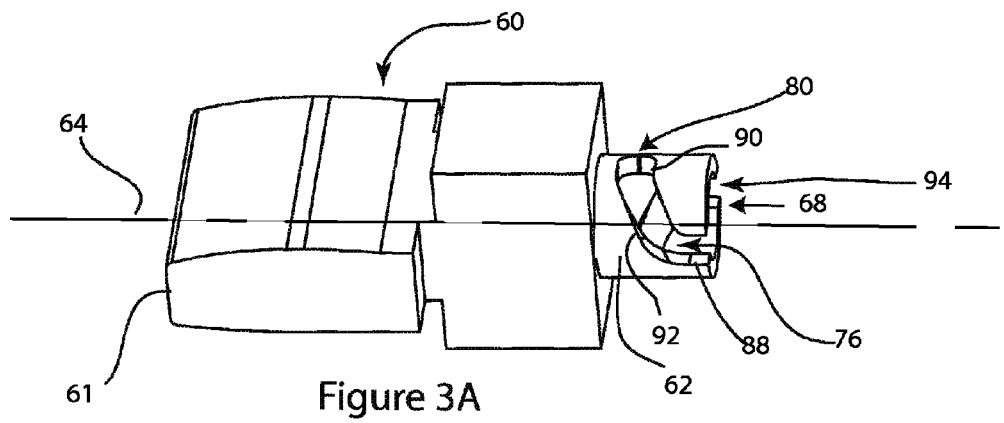
FIG. 3A is a perspective cephalad-lateral view of the spinal trial implant of FIG. 1.
Figure 3B:
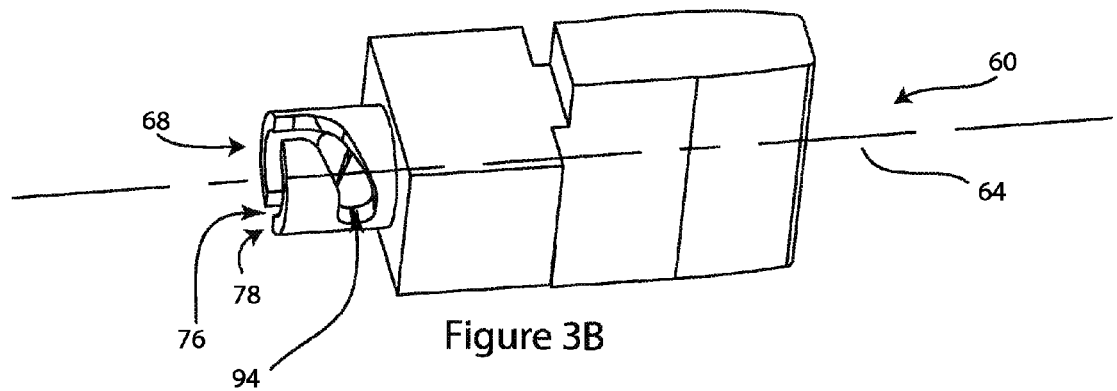
FIG. 3B is a perspective caudal-lateral view of the spinal trial implant of FIG. 1.
Figure 3C:
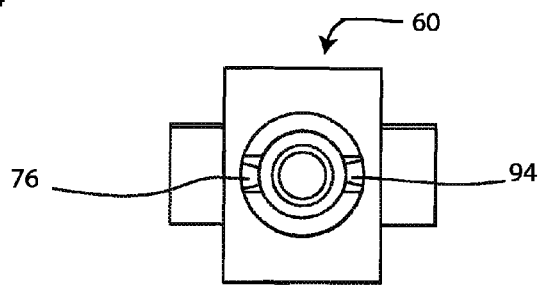
FIG. 3C is an anterior view of the spinal trial implant of FIG. 1.

The first slot 76 may have a starting end 78 at the open end 68 and a terminal end 80 spaced apart from the open end 68. The starting end 78 provides an opening, or mouth, through the open end 68 into the first slot 76. The terminal end 80 may be a blind end, or terminus. The terminal end 80 has a combined offset from the starting end 78, with a first component of the offset in a direction parallel to the axis 64, and a second component of the offset in an angular direction around the axis 64. In the embodiment of FIGS. 3A-C, the angular offset is about 90 degrees, although other angular offsets are contemplated.

The first slot 76 may have a starting portion 88 that extends parallel to the axis 64 and a terminal portion 90 that extends perpendicular to the axis 64. The first slot 76 may also have a helical portion 92 between the starting end 78 and the terminal end 80. The helical portion 92 spirals around the side wall 74 of the socket 62 in a manner similar to a screw thread.

The socket 62 may include a second slot 94 like the first slot 76. The second slot 94 may be in a position that is rotated around the axis 64 relative to the first slot 76. Thus, the first slot 76 and the second slot 94 may be arranged in a circular array around the axis 64. In FIGS. 3A-C, the second slot 94 is in a position that is rotated 180 degrees from the first slot 76, so that the slots 76, 94 are symmetrically arranged around the axis 64 on opposite sides of the socket 62.

With reference to FIGS. 2 and 3A-C, one may appreciate that the pins 20, 32 and the slots 76, 94 are advantageously arranged in complementary circular arrays.

The socket 62 may be fabricated from polymers, metals, ceramics, composites, glass, wood, or other materials according to the requirements of a particular application. The socket 62 may be fabricated from a combination of materials, so that each feature of the socket 62 is fabricated from a material suitable to the particular requirements of the individual feature. In the context of surgical instruments, implants, and systems, it is contemplated that the socket 62 may be fabricated from polymers such as polyetheretherketone (PEEK), acetal, or ultra high molecular weight polyethylene (UHMWPE), or from metals comprising iron, chrome, titanium, nickel, or molybdenum.

An alternate embodiment shaft 112 is shown in FIGS. 7A-D. Shaft 112 is similar to shaft 12 of tool 10, but shaft 112 only includes features which cooperate with a socket to form a connection mechanism. Shaft 112 may thus be described as a subcomponent or design element which could be incorporated into the design of a more fully featured component. For example, shaft 112 may be incorporated onto a working end of a shaft of a nut driver for nuts incorporating a cooperating socket (described below). As another example, shaft 112 may be incorporated onto a stem of a tibial trial component for removably attaching modular trial stems incorporating a cooperating socket.

Shaft 112 may have an axis 114, an outer diameter 116, a tip end 118, two pins 120, 132, two cantilever bodies 122, 124, a slit 126, two bosses 128, 130, four flattened portions 134, 136, 138, 140, two flattened regions 142, 144, and a bevel 146. All of these features are identical to the corresponding features described for shaft 12.

FIGS. 12A-F illustrate additional shaft embodiments, each of which shares at least some features in common with shafts 12, 112. The following descriptions disclose distinguishing characteristics of each embodiment.

Figure 12A:
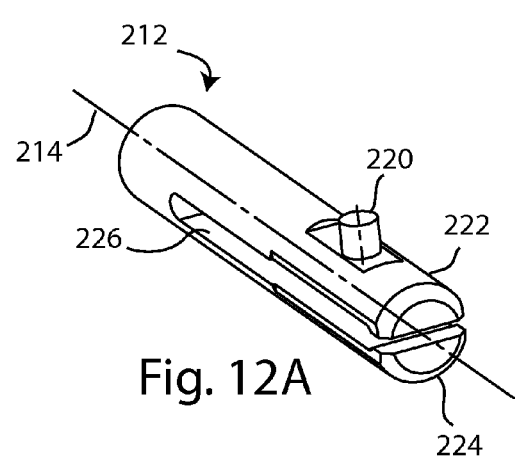
FIG. 12A is a perspective view of another shaft, with two cantilever bodies and one pin.

Shaft 212 of FIG. 12A may have a longitudinal center axis 214, two cantilever bodies 222, 224, a slit 226, and a single pin 220. Pin 220 is carried by cantilever body 222, and slit 226 is orthogonal to pin 220.

Figure 12B:
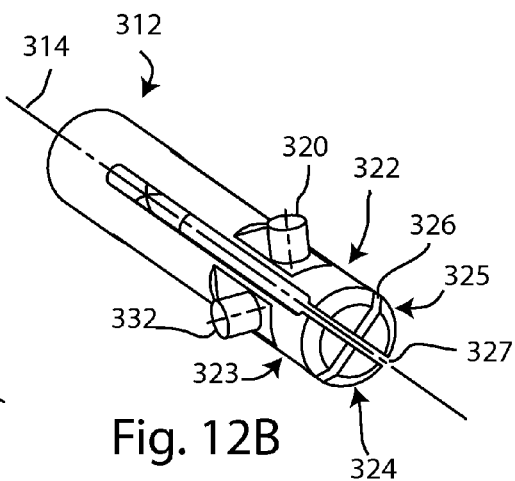
FIG. 12B is a perspective view of yet another shaft, with four cantilever bodies and two adjacent pins.

Shaft 312 of FIG. 12B may have a longitudinal center axis 314, four cantilever bodies 322, 323, 324, 325, two slits 326, 327, and two pins 320, 332. Pin 320 is carried by cantilever body 322 and pin 332 is carried by cantilever body 323, so that pins 320, 332 are asymmetrically arranged about axis 314. Slits 326 and 327 are identical, and are oriented at 45 degree angles to pins 320, 332. Shaft 312 lacks a flattened portion, comparable to flattened portion 34, along any of the cantilever bodies 322, 323, 324, 325.

Figure 12C:
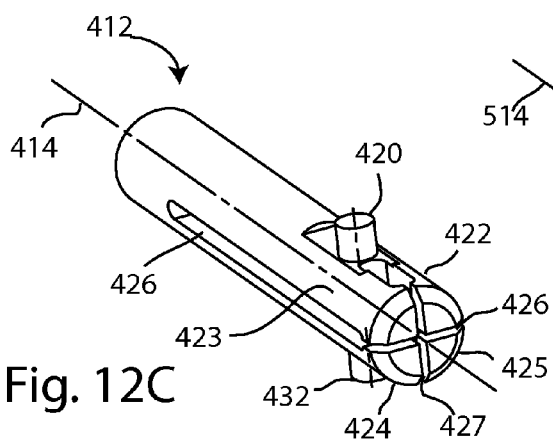
FIG. 12C is a perspective view of yet another shaft, with four cantilever bodies and two opposite pins.

Shaft 412 of FIG. 12C may have a longitudinal center axis 414, four cantilever bodies 422, 423, 424, 425, two slits 426, 427, and two pins 420, 432. Slit 426 is similar in design to slit 26. Slit 427 terminates beside pins 420, 432 so that slit 427 is much shorter than slit 426. Slit 426 is orthogonal to pins 420, 432, while slit 427 is parallel to pins 420, 432. Pin 420 is carried at the juncture of cantilever bodies 422, 423 and pin 432 is carried at the juncture of cantilever bodies 424, 425, so that pins 420, 432 are symmetrically arranged about axis 414. Shaft 412 lacks a flattened portion, comparable to flattened portion 34, along any of the cantilever bodies 422, 423, 424, 425.

Figure 12D:
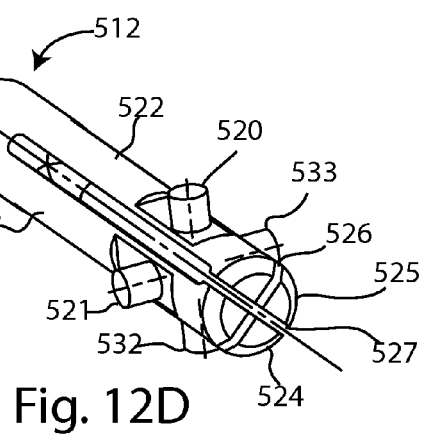
FIG. 12D is a perspective view of yet another shaft, with four cantilever bodies and four pins.

Shaft 512 of FIG. 12D may have a longitudinal center axis 514, four cantilever bodies 522, 523, 524, 525, two slits 526, 527, and four pins 520, 521, 532, 533. Pin 520 is carried by cantilever body 522, pin 521 is carried by cantilever body 523, pin 532 is carried by cantilever body 524, and pin 533 is carried by cantilever body 525, so that pins 520, 521, 532, 533 are symmetrically arranged about axis 514. Slits 526 and 527 are identical, and are oriented at 45 degree angles to pins 520, 532. Shaft 512 lacks a flattened portion, comparable to flattened portion 34, along any of the cantilever bodies 522, 523, 524, 525.

Figure 12E:
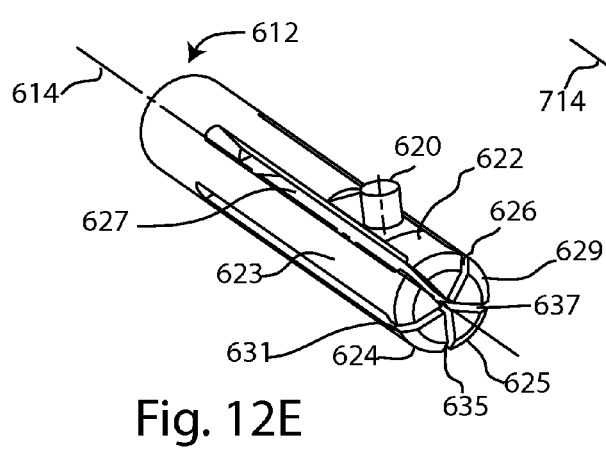
FIG. 12E is a perspective view of yet another shaft, with five cantilever bodies and one pin.

Shaft 612 of FIG. 12E may have a longitudinal center axis 614, five cantilever bodies 622, 623, 624, 625, 629, five slits 626, 627, 631, 635, 637, and a single pin 620. Pin 620 is carried by cantilever body 622. Slits 626, 627, 631, 635, 637 are identical, extending only halfway through shaft 612. Slits 626, 627 are oriented at 36 degree angles to pin 620, and all five slits 626, 627, 631, 635, 637 are symmetrically arranged about axis 614. Shaft 612 lacks a flattened portion, comparable to flattened portion 34, along any of the cantilever bodies 622, 623, 624, 625, 629.

Figure 12F:
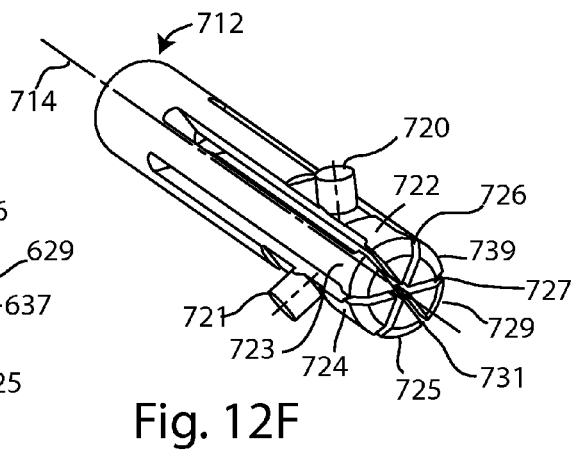
FIG. 12F is a perspective view of yet another shaft, with six cantilever bodies and three pins.

Shaft 712 of FIG. 12F may have a longitudinal center axis 714, six cantilever bodies 722, 723, 724, 725, 729, 739, three slits 726, 727, 731, and three pins 720, 721, 732. Pin 720 is carried by cantilever body 722, pin 721 is carried by cantilever body 724, and pin 732 (obscured by remainder of shaft 712) is carried by cantilever body 729, so that pins 720, 721, 732 are symmetrically arranged about axis 714. Shaft 712 lacks a flattened portion, comparable to flattened portion 34, along any of the cantilever bodies 722, 723, 724, 725, 729, 739.

Any of the pins described herein may alternatively protrude from the corresponding shaft in a direction other than normal to the corresponding outer diameter and/or in a direction other than orthogonal to the corresponding axis. Any of the pins described herein may alternatively have a non-circular cross sectional shape, such as triangle, oval, elliptical, polygonal, teardrop, or lobed. Such cross sectional shapes may cause the pin to resemble a tab, ear, flange, or post instead of a cylinder.

The tip end of a shaft may have a single cantilever body, or may be split into two or more cantilever bodies according to the needs of a particular application. FIGS. 12B-F show embodiments having different numbers of cantilever bodies. The tip end may have slits that extend partially or entirely across the shaft in order to form the desired number of cantilever bodies. FIG. 12E shows an embodiment with slits that extend partially across shaft 612, while FIGS. 12A-D and F show embodiments with slits that extend entirely across the corresponding shaft.

Pins may be arranged around a shaft in a symmetric or asymmetric circular array. FIGS. 12C, D, and F illustrate symmetrical pin arrays, while FIG. 12B illustrates an asymmetric pin array. Pins may all be alike, so that a shaft may have a single array of pins. Alternatively, a shaft may have a plurality of arrays, wherein each array is characterized by a different pin configuration. For example, one such embodiment may include two pin configurations which alternate around an outer diameter of a shaft. Each of the pins may be situated on a separate cantilever body, in a manner reminiscent of FIG. 12D. Alternatively, each cantilever body may carry a plurality of pins. In a further alternative, selected cantilever bodies may lack pins altogether, as illustrated in FIGS. 12A, B, E, and F.

Alternative shaft embodiments may employ edge break configurations that differ from flattened portions 34, 36, 38, 40. These may include features such as chamfers, bull noses, radii, fillets, or variable edge blends. The edge break may be confined to a zone proximate the tip end of a shaft. Edge break may be unnecessary in certain embodiments, such as those shown in FIGS. 12B-F.

A shaft may optionally include a longitudinal through hole or cannulation.

Alternative shaft embodiments may employ edge break configurations that differ from bevel 46. These may include features such as a chamfer, bull nose, radius, fillet, or variable edge blend. Edge break may be unnecessary in certain embodiments.

An alternate embodiment socket 162 is shown in FIGS. 8A-F. Socket 162 is similar to socket 62 of trial 60, but socket 162 only includes features which cooperate with a shaft to form a connection mechanism. Socket 162 may thus be described as a subcomponent or design element which could be incorporated into the design of a more fully featured component. By way of non-limiting example, socket 162 may be incorporated on a working end of a shaft for a screwdriver for use with screws incorporating shaft 112, or socket 162 may be formed into a broach for use with a broaching handle incorporating shaft 112.

Socket 162 may have an inner diameter 166, an open end 168, a second end 170, a tapered region 172, a side wall 174, a first slot 176, a starting end 178, a terminal end 180, a starting portion 188, a terminal portion 190, a helical portion 192, and a second slot 194. All of these features are identical to the corresponding features described for socket 62.

FIGS. 13A-J illustrate additional socket embodiments, each of which shares at least some features in common with sockets 62, 162. The following descriptions disclose distinguishing characteristics of each embodiment.

Figure 13A:
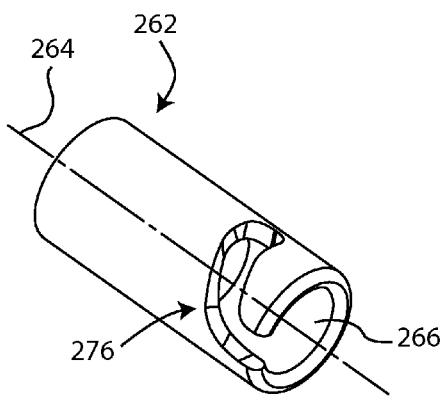
FIG. 13A is a perspective view of another socket, with one slot having a starting portion, a helical portion, and a terminal portion.
Figure 13B:
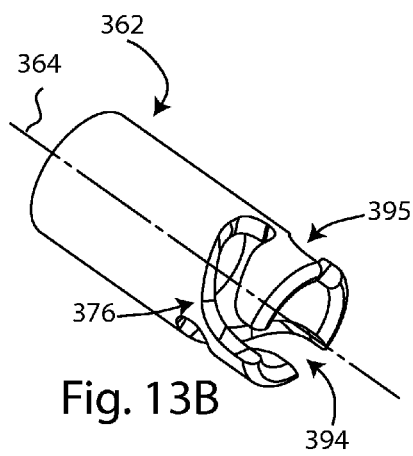
FIG. 13B is a perspective view of yet another socket, with three slots like the slot in FIG. 13A.
Figure 13C:
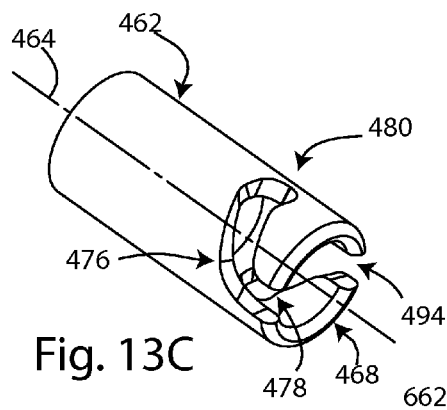
FIG. 13C is a perspective view of yet another socket, with two slots, each having a starting portion, a helical portion, and a terminal portion.
Figure 13D:
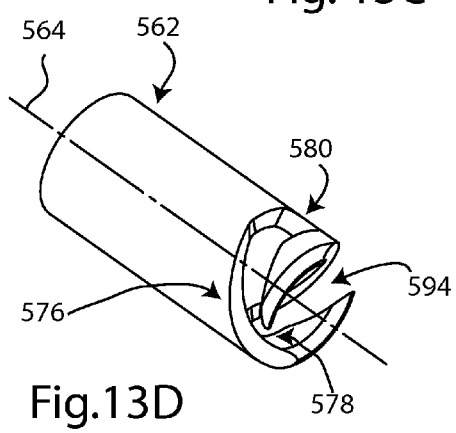
FIG. 13D is a perspective view of yet another socket, with two slots, each having a helical portion and a terminal portion.
Figure 13E:
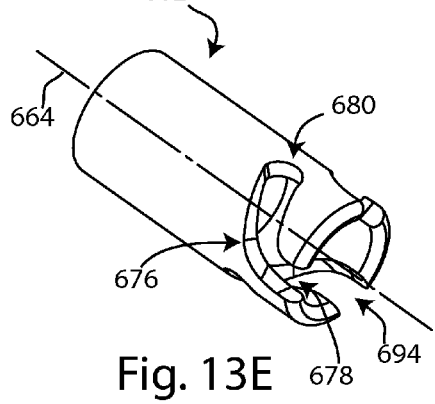
FIG. 13E is a perspective view of yet another socket, with two slots, each having a starting portion and a helical portion.
Figures 13F, 13G:
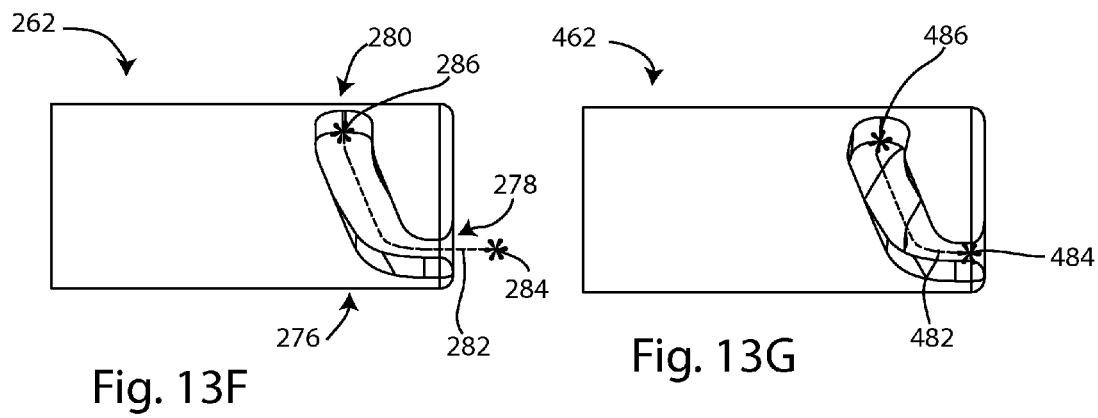
FIG. 13F is a front view of the socket of FIG. 13A.
FIG. 13G is a front view of the socket of FIG. 13C.

Socket 262 of FIGS. 13A and 13F may have a longitudinal center axis 264 and a single slot 276. Slot 276 is identical to slot 76. Slot 276 follows a path 282 between a starting end 278 and a terminal end 280. The path 282 may extend between a starting point 284 and a terminal point 286. The starting point 284 may be at the starting end 278 or at a location outside the open end 268. The terminal point 286 may be at or near the terminal end 280. The terminal point 286 may be offset from the starting point 284 along the longitudinal axis 264 and around the inner diameter 266, in order to produce a desired combined offset for the terminal end 280. The path 282 may describe a tool path followed by a cutter during fabrication of the slot 276.

Socket 362 of FIG. 13B may have a longitudinal center axis 364 and three slots 376, 394, 395. Each of the slots 376, 394, 395 is identical to slot 76. The slots 376, 394, 395 are symmetrically arranged around axis 364.

Socket 462 of FIGS. 13C and 13G may have a longitudinal center axis 464, an open end 468, and two identical slots 476, 494 symmetrically arranged around axis 464 on opposite sides of socket 462. Slot 476 extends between a starting end 478 and a terminal end 480. Slot 476 follows a path 482 between a starting point 484 and a terminal point 486. The path 482 resembles path 282, but a portion of the path 482 between the starting point 484 and the terminal point 486 is spaced farther from the open end 468 than is the terminal point 486, as is best appreciated in FIG. 13G. As a result, slot 476 extends along the socket 462 past the location of the terminal end 480, and then turns back to reach the terminal end 480.

Figures 13H, 13J:
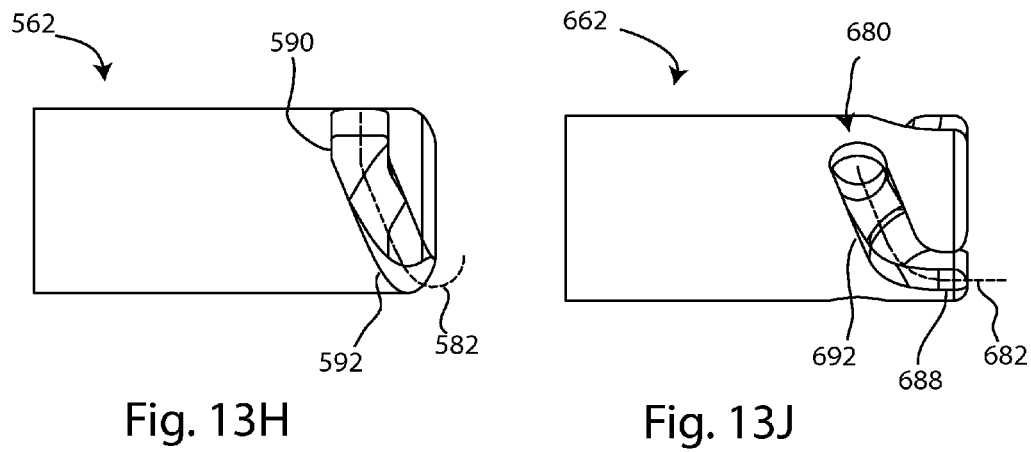
FIG. 13H is a front view of the socket of FIG. 13D.
FIG. 13J is a front view of the socket of FIG. 13E.

Socket 562 of FIGS. 13D and 13H may have a longitudinal center axis 564 and two identical slots 576, 594 symmetrically arranged around axis 564 on opposite sides of socket 562. Slot 576 extends between a starting end 578 and a terminal end 580. Slot 576 may have a terminal portion 590 like terminal portion 90 and a helical portion 592 like helical portion 92. However, slot 576 lacks a starting portion like starting portion 88. Instead, helical portion 592 extends all the way to the starting end 578 along path 582.

Socket 662 of FIGS. 13E and 13J may have a longitudinal center axis 664 and two identical slots 676, 694 symmetrically arranged around axis 664 on opposite sides of socket 662. Slot 676 extends between a starting end 678 and a terminal end 680. Slot 676 may have a starting portion 688 like starting portion 88 and a helical portion 692 like helical portion 92. However, slot 676 lacks a terminal portion like terminal portion 90. Instead, helical portion 692 extends all the way to the terminal end 680 along path 682.

FIGS. 14A-G illustrate additional socket embodiments, each of which shares at least some features in common with sockets 62, 162. The following descriptions disclose distinguishing characteristics of each embodiment.

Figure 14A:
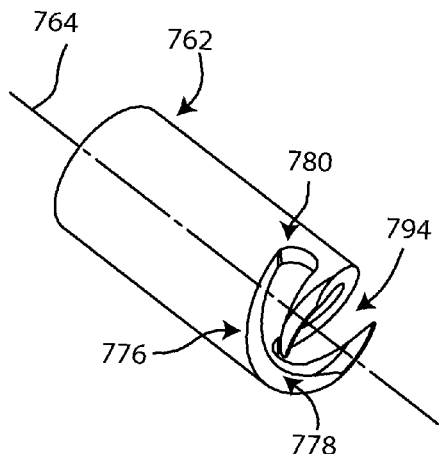
FIG. 14A is a perspective view of yet another socket, with two slots, each having a helical portion.
Figure 14B:
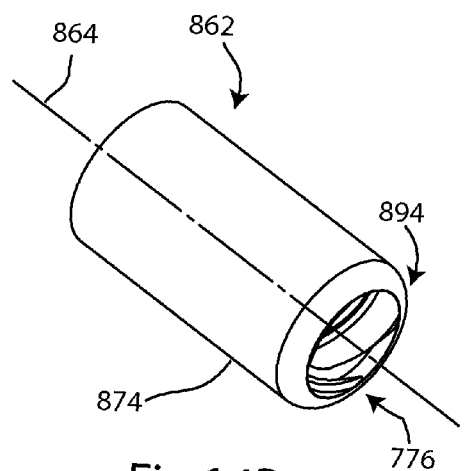
FIG. 14B is a perspective view of yet another socket, with two slots like the slots in FIG. 14A extending partially through a side wall of the socket.
Figure 14C:
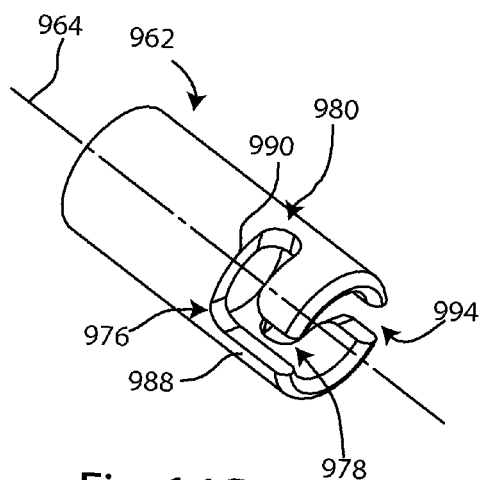
FIG. 14C is a perspective view of yet another socket, with two slots, each having a starting portion and a terminal portion.
Figure 14D:
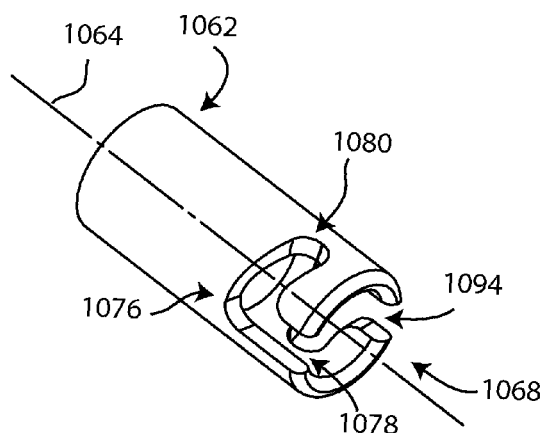
FIG. 14D is a perspective view of yet another socket, with two slots, each having a starting portion and a terminal portion.
Figure 14E:
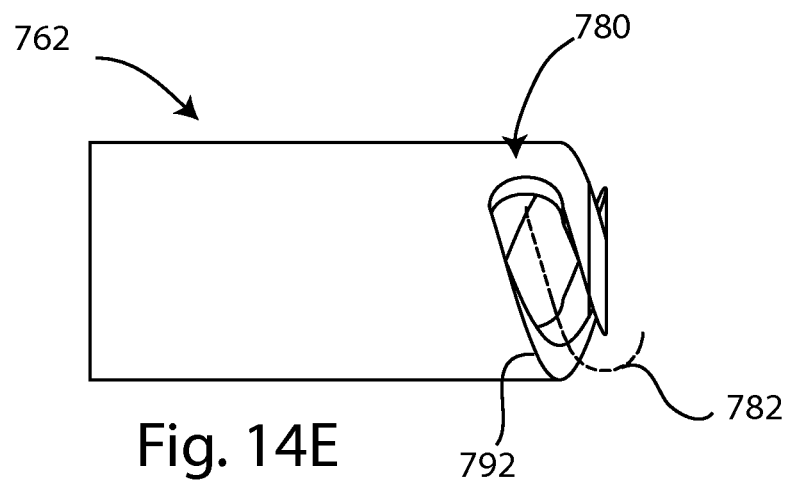
FIG. 14E is a front view of the socket of FIG. 14A.

Socket 762 of FIGS. 14A and 14E may have a longitudinal center axis 764 and two identical slots 776, 794 symmetrically arranged around axis 764 on opposite sides of socket 762. Slot 776 extends between a starting end 778 and a terminal end 780. Slot 776 may have a helical portion 792 like helical portion 92. However, slot 776 lacks a starting portion like starting portion 88. Slot 776 also lacks a terminal portion like terminal portion 90. Instead, helical portion 792 extends all the way to the terminal end 780 along path 782.

Socket 862 of FIG. 14B may have a longitudinal center axis 864 and two identical slots 876, 894 symmetrically arranged around axis 864 on opposite sides of socket 862. Slots 876, 894 are identical to slots 776, 794. However, slots 876, 894 project only partially through a side wall 874 of socket 862, so that socket 862 possesses a smooth, continuous outer surface. This embodiment may afford greater strength to slots 876, 894 in service, and may be less likely to snag on surrounding objects.

Figure 14F:
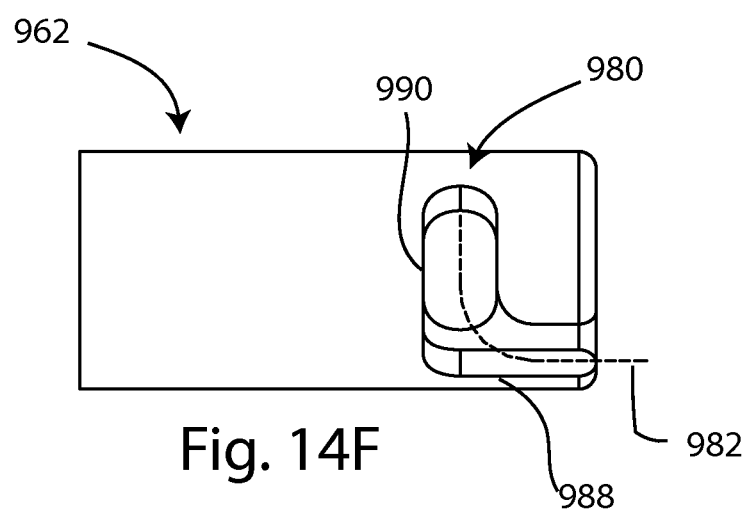
FIG. 14F is a front view of the socket of FIG. 14C.

Socket 962 of FIGS. 14C and 14F may have a longitudinal center axis 964 and two identical slots 976, 994 symmetrically arranged around axis 964 on opposite sides of socket 962. Slot 976 extends between a starting end 978 and a terminal end 980. Slot 976 may have a starting portion 988 like starting portion 88 and a terminal portion 990 like terminal portion 90. However, slot 976 lacks a helical portion like helical portion 92. Instead, starting portion 988 blends directly into terminal portion 990 along path 982.

Figure 14G:
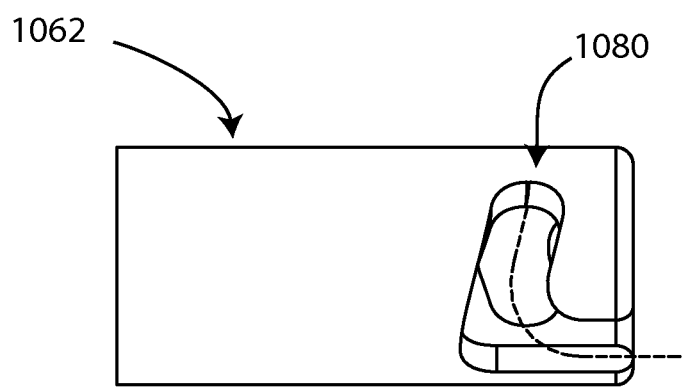
FIG. 14G is a front view of the socket of FIG. 14D.

Socket 1062 of FIGS. 14D and 14G may have a longitudinal center axis 1064, an open end 1068, and two identical slots 1076, 1094 symmetrically arranged around axis 1064 on opposite sides of socket 1062. Slot 1076 extends between a starting end 1078 and a terminal end 1080. Slot 1076 resembles slot 976. However, a portion of slot 1076 lies farther from the open end 1068 than does the terminal end 1080, as is best seen in FIG. 14G.

In alternative embodiments, a socket may have a hole or cannulation (not shown) extending from a second end of the socket. The hole or cannulation may go partially or completely through the socket. The second end may simply be an intersection, or edge, between a tapered region within the socket and a hole extending farther into the socket.

Slots and their corresponding paths may be configured in various ways. A terminal portion of a slot may make an angle of precisely 90 degrees with respect to a corresponding axis. FIGS. 3A-C, 8D, 13F, and 14F show examples of this type of terminal portion. Alternatively, it may be advantageous for a terminal portion to make an acute angle with respect to the axis. For example, the terminal portion may hook back toward the open end of the socket, as is shown in FIGS. 13G and 14G. Starting and terminal portions of a slot may be separated by one or more intervening portions, such as a helical portion (FIGS. 13A and F) or a non-helical ramp. Alternatively, the starting portion may transition directly to the terminal portion so that the slot more closely resembles an "L" or a dogleg configuration, as illustrated in FIGS. 14 C, D, F, and G. It is further contemplated that a starting portion could combine with dual terminal portions to form a "T" configuration.

In further embodiments, a slot may be made up of multiple portions or segments so that a shaft and a socket may be locked together with varying degrees of security, or in multiple orientations and positions.

In other embodiments, a slot may terminate in a recessed portion into which a pin must be forced against friction. An embodiment with this characteristic may provide additional locking force to couple a shaft and a socket together.

In alternate embodiments, a socket may have a plurality of slots arranged in a circular array around a longitudinal center axis of the socket. The plurality of slots may be arranged symmetrically or asymmetrically. The slots may all be alike, so that the socket may have a single array of slots. Alternatively, the socket may have a plurality of arrays, wherein each array is characterized by a different slot configuration. For example, one such embodiment may include two slot configurations which alternate around a side wall of the socket.

The number and arrangement of pins on a shaft need not exactly match the number and arrangement of slots on a corresponding socket. Rather, it is sufficient that the number and arrangement of pins on the shaft coordinates with the number and arrangement of slots on the socket to provide the desired number of mating orientations between the shaft and the socket. By way of non-limiting example, a shaft having only one pin may provide two mating orientations with a socket having two slots. A shaft with two pins may provide six mating orientations with a socket having six slots. A shaft having a larger first pin and a smaller second pin may provide one mating orientation with a socket having a larger first slot and a smaller second slot.

The embodiment shown in FIGS. 1-6 is configured for assembly of the shaft 12 to the socket 62. The inner diameter 66 of the socket 62 is larger than the outer diameter 16 of the shaft 12, such that the outer diameter 16 fits within the inner diameter 66. The first and second slots 76, 94 are larger than the first and second pins 20, 32, respectively, such that the first and second pins 20, 32 fit within the first and second slots 76, 94, respectively.

Figure 5:
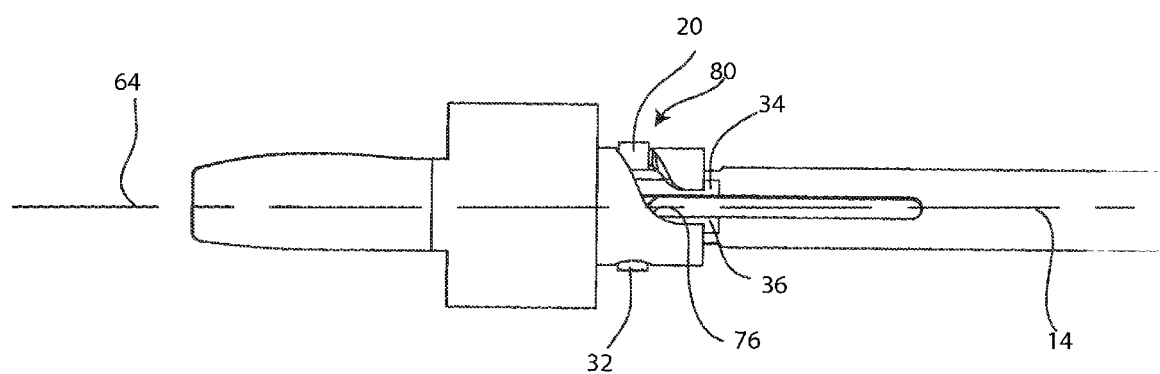
FIG. 5 is a lateral view of the spinal trial implant and inserter tool of FIG. 1, with the inserter tool fully locked to the spinal trial implant.
Figure 6:
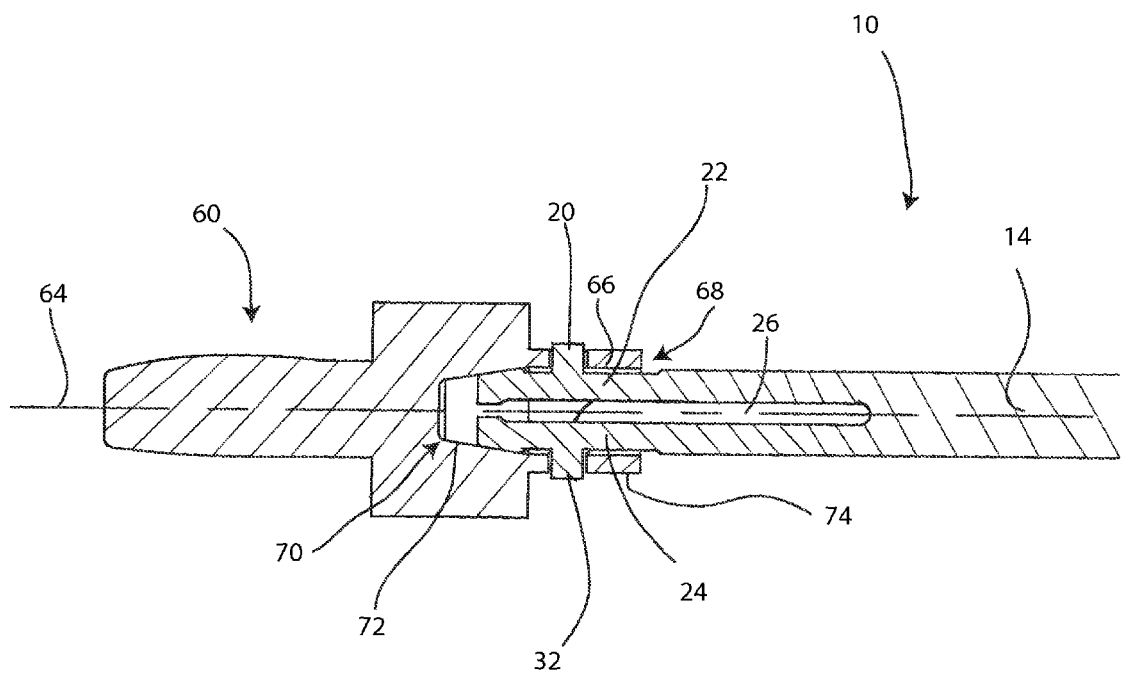
FIG. 6 is a cross-sectional view of the spinal trial implant and inserter tool of FIG. 5.
Figure 8E:
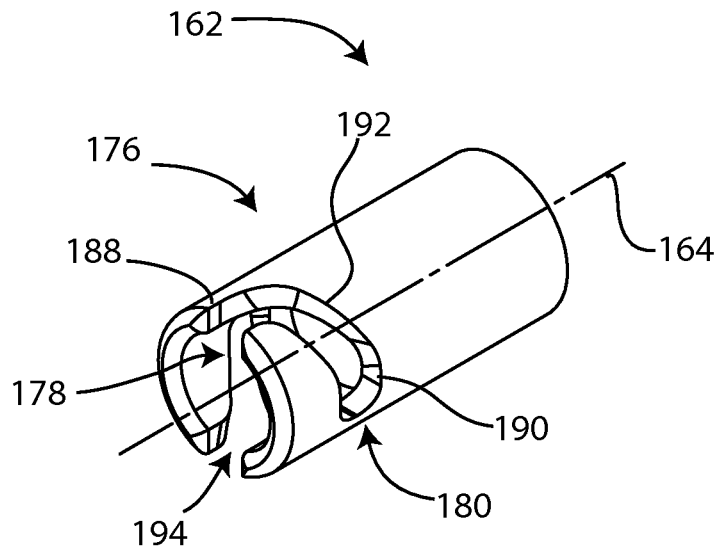
FIG. 8E is a front perspective view of the socket of FIG. 8A.
Figure 8F:
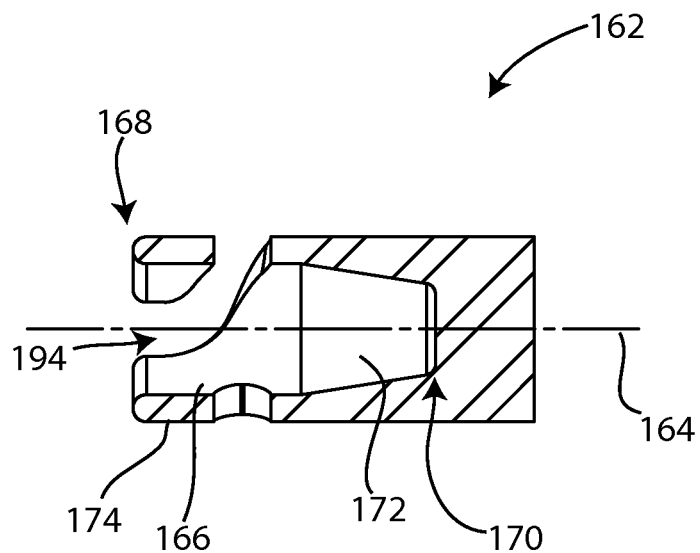
FIG. 8F is a cross sectional view of the socket of FIG. 8A taken along the section line indicated in FIG. 8D.

The shaft 12 is selectively movable, relative to the socket 62, between an unlocked position and a locked position. FIG. 4 illustrates the unlocked position. FIGS. 5-6 illustrate the locked position. In the unlocked position, the shaft 12 and the socket 62 are freely separable. In the locked position, the shaft 12 and the socket 62 are secured together sufficiently to resist service loads. One can appreciate that the security of the locked position for a specific application may be directly proportional to the magnitude of service loads in that application.

In the unlocked position of FIG. 4, the axes 14, 64 are substantially aligned, the tip end 18 is positioned in the inner diameter 66, and the first pin 20 is positioned in the starting end 78, or mouth, of the first slot 76. In the embodiment of FIGS. 1-6, the second pin 32 is also in a starting end of the second slot 94 in the unlocked position. In alternate embodiments comprising a plurality of pins and slots, one can appreciate that some or all of the pins may be in starting ends of corresponding slots.

In the locked position of FIGS. 5-6, the axes 14, 64 are substantially aligned, the tip end 18 is wedged in the tapered region 72 so as to at least partially pinch the slit 26 closed, and the first pin 20 is in the terminal end 80, or terminus, of the first slot 76. Thus, the cantilever bodies 22, 24 are at least partially compressed together. The flattened portions 34, 36, 38, 40 provide relief across the incompressible width of the cantilever bodies 22, 24 so that there is clearance with the tapered region 72. The bevel 46, if present, may be complementary to the tapered region 72. In the embodiment of FIGS. 1-6, the second pin 32 is also in a terminal end of the second slot 94. In alternate embodiments comprising a plurality of pins and slots, one can appreciate that some or all of the pins may be in terminal ends of corresponding slots. Furthermore, the sort of relief provided by flattened portions 34, 36, 38, 40 may not be necessary in alternative embodiments with narrow cantilever bodies, such as embodiments comprising three or more cantilever bodies.

Any material possesses inherent material properties. Material properties may be modified through manufacturing processes such as heat treatment, work hardening, pressure treatments, or aging. By way of non-limiting example, a material may be characterized by an elastic limit. The elastic limit is a stress at which the material begins to experience plastic, or permanent, deformation. At stresses below the elastic limit, the material experiences elastic, or temporary, deformation which spontaneously resolves as soon as applied forces are removed. For example, the shaft 12 may be designed so that stresses in the shaft 12 due to deformation of the cantilever bodies 22, 24 are less than the elastic limit when the tip end 18 is wedged in the tapered region 72 so as to pinch the slit 26 completely closed at the tip end 18. This may be accomplished by designing a specific clearance, or gap, between bosses 28, 30, so that the bosses 28, 30 contact each other and thereby prevent further deformation of the cantilever bodies 22, 24. Slit 26 may be advantageously designed in view of the material properties resulting after completion of all applicable manufacturing operations.

In the locked position, the shaft 12 and socket 62 are secured together by frictional forces. At least some of the frictional forces may result from elastic deformation of the cantilever bodies 22, 24 when the tip end 18 wedges into the tapered region 72.

A first frictional force may exist where the tip end 18 is wedged into the tapered region 72. The cantilever bodies 22, 24 tend to resist being compressed together. Thus, the tip end 18 exerts a force against the tapered region 72, acting in a direction generally normal to the contacting surfaces. This outward normal force causes the first frictional force, which resists rotation of the tip end 18 against the tapered region 72.

A second frictional force may exist where the first pin 20 rests within the terminal end 80 of the first slot 76. The second frictional force may be related to the first frictional force. The tip end 18 tends to resist wedging into the tapered region 72. At least a portion of such resistance may act along the axes 14, 64 so as to force the first pin 20 against a side of the first slot 76 opposite the tapered region 72, i.e., a side closer to the open end 68. The force between the first pin 20 and the side of the first slot 76 acts in a direction generally normal to the contacting surfaces. This axial normal force causes the second frictional force, which resists sliding of the first pin 20 along the side of the first slot 76. One can appreciate that a similar frictional force may exist between other pins and slots in alternate embodiments.

The second frictional force may alternatively be caused by other interactions between features of the shaft 12 and the socket 62, such as wedging of the first pin 20 into an undercut, a recessed region, or a tapered constriction proximate the terminal end 80 of the first slot 76. Furthermore, additional frictional forces may be present in alternative embodiments.

With reference to FIGS. 4-6, the shaft 12 is selectively movable between the unlocked and locked positions by rotating the shaft 12 within the socket 62 so that the first pin 20 slides along the first slot 76 between the starting and terminal ends 78, 80. In the present embodiment, clockwise rotation of the shaft 12 in the socket 62 moves the shaft 12 from the unlocked position of FIG. 4 to the locked position of FIGS. 5-6. Counterclockwise rotation of the shaft 12 in the socket 62 moves the shaft 12 from the locked position of FIGS. 5-6 to the unlocked position of FIG. 4. In an alternate embodiment, these rotational directions may be reversed.

As the shaft 12 moves between the unlocked position and the locked position, the first pin 20 slides along the first slot 76 between the starting and terminal ends 78, 80. Thus, the specific configuration of the first slot 76 dictates the motion of the shaft 12 relative to the socket 62. By way of non-limiting example, the starting portion 88 of the first slot 76 of FIGS. 4-6 guides the shaft 12 into the socket 62 in a direction generally parallel to the axes 14, 64. The starting portion 88 prevents rotation of the pin 20 about the axes 14, 64. The helical portion 92 constrains the shaft 12 to rotate clockwise about the axes 14, 64 and simultaneously advance within the socket 62 in a direction generally parallel to the axes 14, 64. The terminal portion 90 permits the shaft 12 to rotate clockwise about the axes 14, 64. Axial advancement is prevented.

The shaft 12 may be selectively movable, relative to the socket 62, to an intermediate position in which the tip end 18 makes incipient contact with the tapered region 72, the slit 26 is uncompressed, the cantilever bodies 22, 24 are undeflected, and the first pin 20 is in the first slot 76 between the starting and terminal ends 78, 80. The intermediate position may be described as a transitional position between the loose unlocked position and the secure locked position.

As the shaft 12 moves from the intermediate position to the locked position, one or more of the aforementioned frictional forces builds between the shaft 12 and the socket 62 to bind the shaft 12 and socket 62 together. As the shaft 12 moves from the locked position to the intermediate position, the friction diminishes so that the shaft 12 and socket are mutually separable.

The embodiment shown in FIGS. 7-11 is configured so that shaft 112 may be assembled, or connected, to socket 162. The inner diameter 166 of the socket 162 receives the outer diameter 116 of the shaft 112 with clearance. The slots 176, 194 of the socket 162 receive the pins 120, 132 of the shaft 112 with clearance.

The shaft 112 is selectively movable, relative to the socket 162, between an unlocked position, illustrated in FIGS. 9A-E, and a locked position, illustrated in FIGS. 11A-E. In the unlocked position, the shaft 112 and socket 162 are freely separable. In the locked position, the shaft 112 and socket 162 are secured together sufficiently to resist service loads. The security of the locked position may be proportional to the magnitude of service loads for a particular application.

Figure 9A:
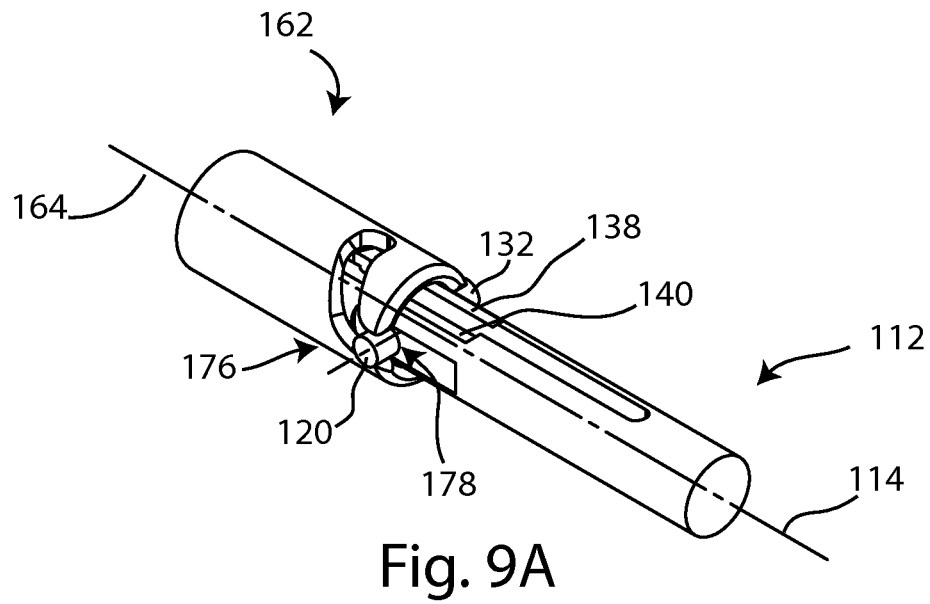
FIG. 9A is a perspective view of the shaft of FIG. 7A in an unlocked position relative to the socket of FIG. 8A.
Figure 9B:
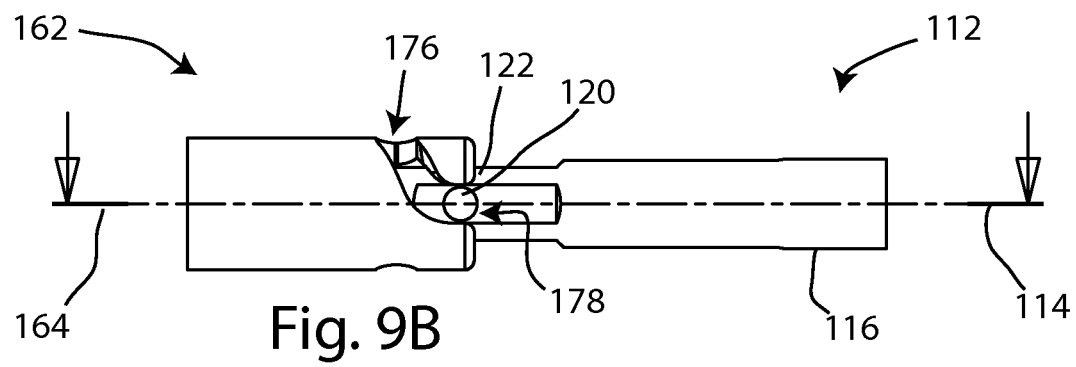
FIG. 9B is a front view of the shaft and socket of FIG. 9A.
Figure 9C:
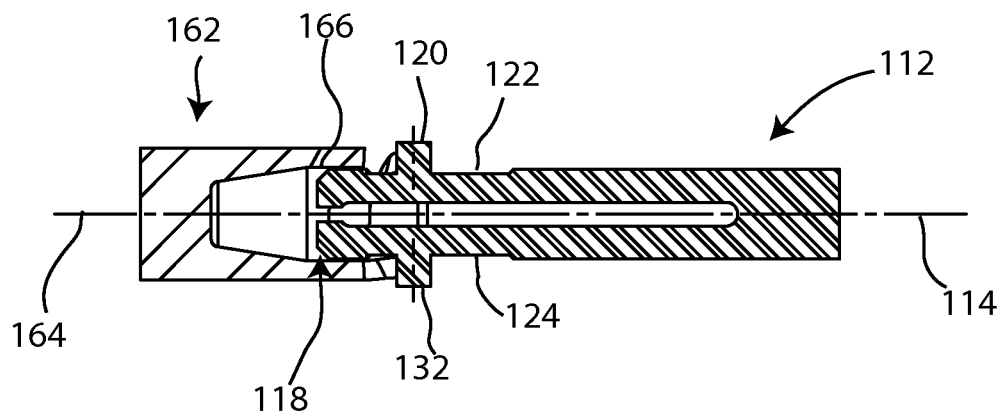
FIG. 9C is a cross sectional view of the shaft and socket of FIG. 9A, taken along the section line shown in FIG. 9B.
Figure 9D:
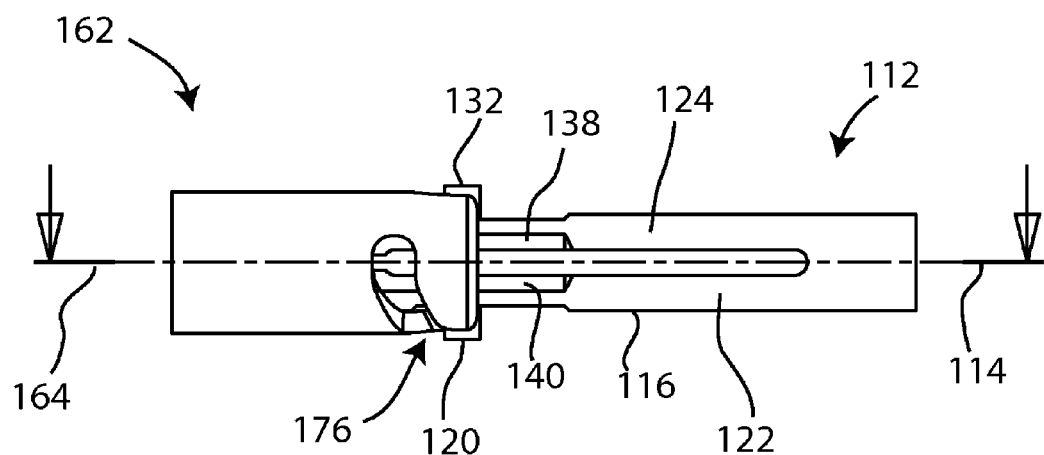
FIG. 9D is a top view of the shaft and socket of FIG. 9A.
Figure 9E:
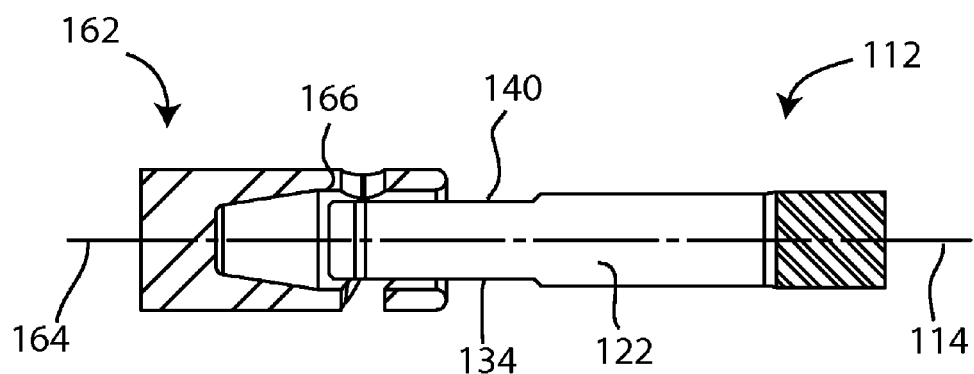
FIG. 9E is a cross sectional view of the shaft and socket of FIG. 9A, taken along the section line shown in FIG. 9D.

In the unlocked position of FIGS. 9A-E, the axes 114, 164 are substantially aligned, the tip end 118 is positioned in the inner diameter 166, and the first pin 120 is positioned in the starting end 178, or mouth, of the first slot 176. In the embodiment of FIGS. 9-11, the second pin 132 is also in a starting end of the second slot 194 in the unlocked position. FIGS. 9C and 9E show mutually perpendicular cross sections through the shaft 112 and socket 162 in the unlocked position. It can be appreciated that outer diameter 116 of shaft 112 is a clearance fit with inner diameter 166 of socket 162, and that flattened portions 134, 136, 138, 140 provide additional clearance across the width of cantilever bodies 122, 124.

Figure 10A:
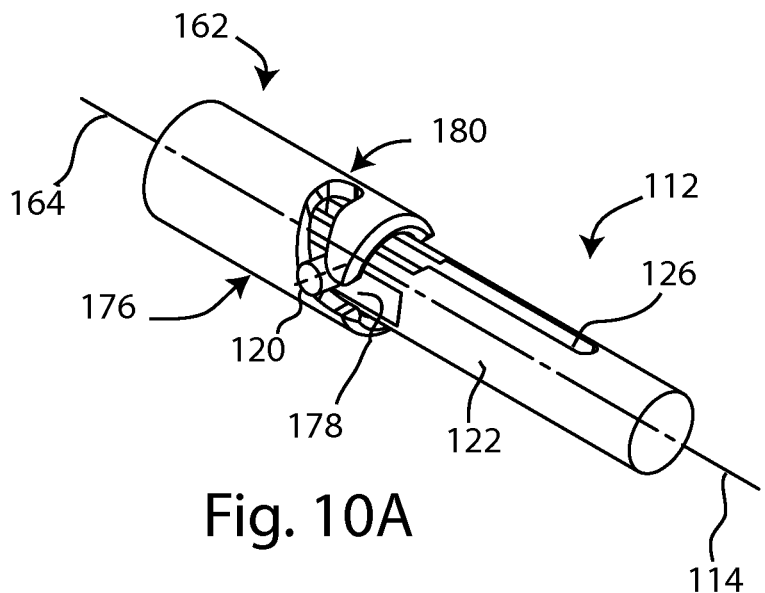
FIG. 10A is a perspective view of the shaft of FIG. 7A in an intermediate position relative to the socket of FIG. 8A.
Figure 10B:
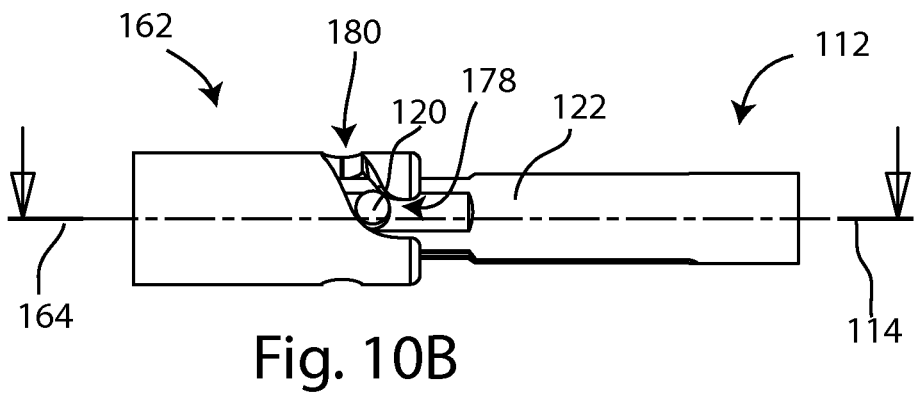
FIG. 10B is a front view of the shaft and socket of FIG. 10A.
Figure 10C:
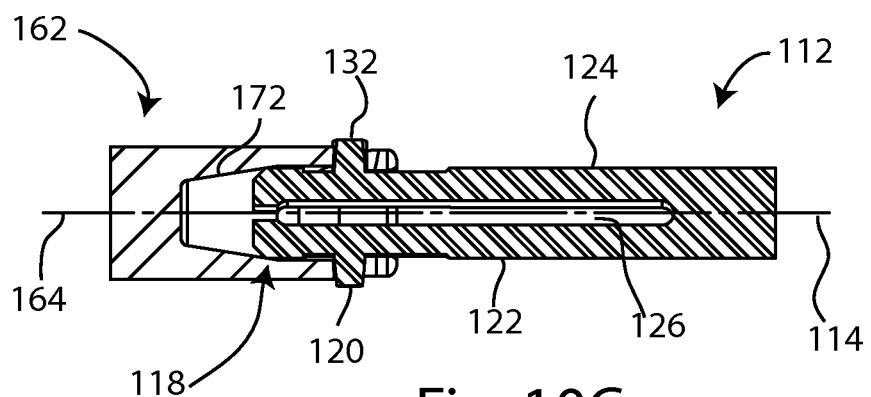
FIG. 10C is a cross sectional view of the shaft and socket of FIG. 10A, taken along the section line shown in FIG. 10B.
Figure 10D:
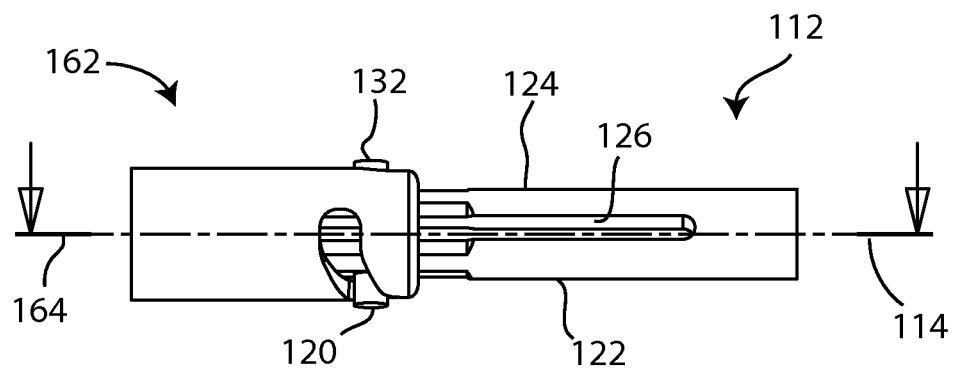
FIG. 10D is a top view of the shaft and socket of FIG. 10A.
Figure 10E:
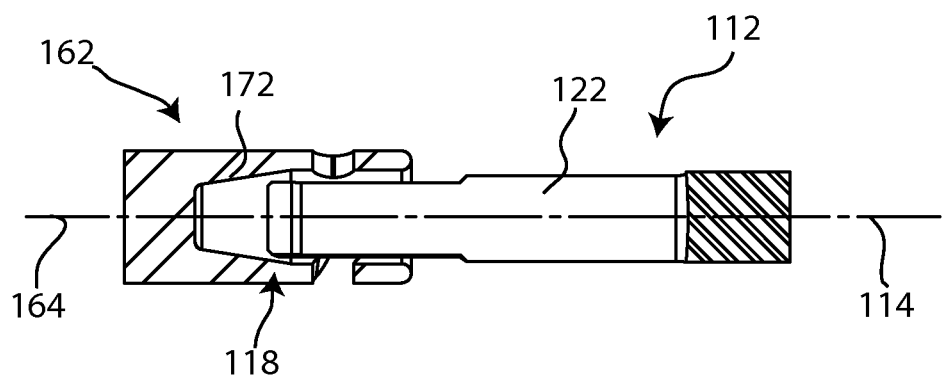
FIG. 10E is a cross sectional view of the shaft and socket of FIG. 10A, taken along the section line shown in FIG. 10D.
Figure 11A:
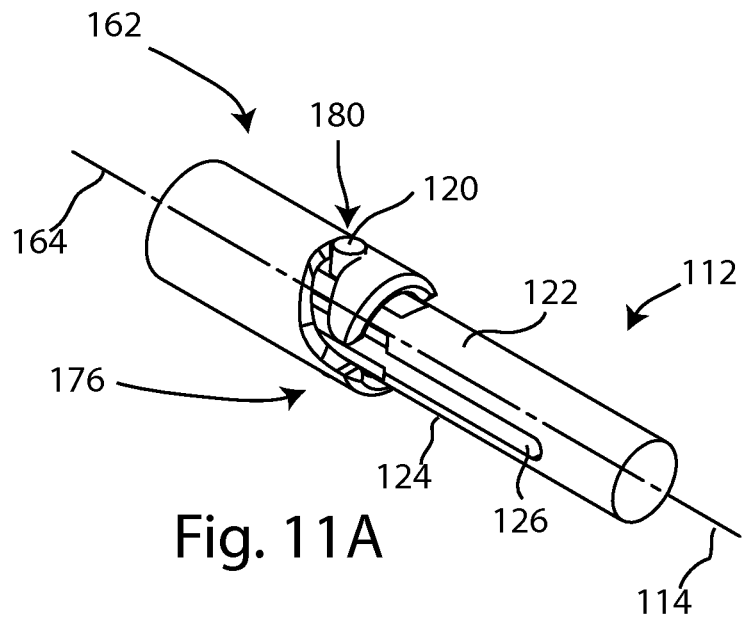
FIG. 11A is a perspective view of the shaft of FIG. 7A in a locked position relative to the socket of FIG. 8A.
Figure 11B:
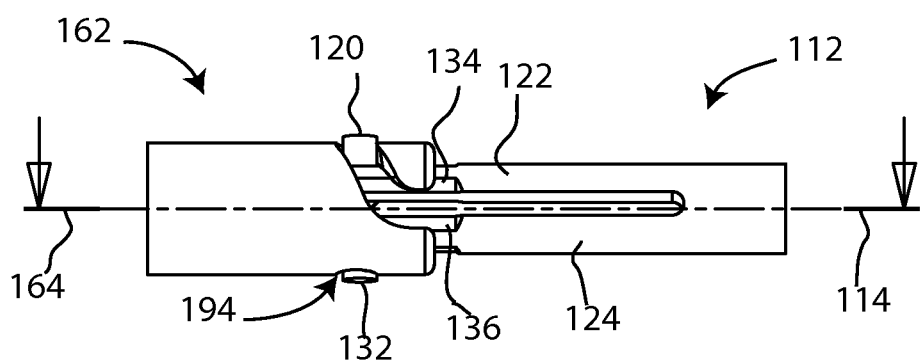
FIG. 11B is a front view of the shaft and socket of FIG. 11A.
Figure 11C:
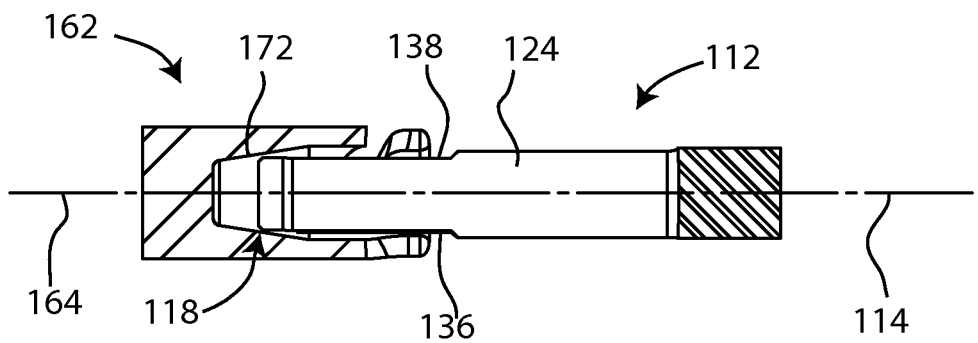
FIG. 11C is a cross sectional view of the shaft and socket of FIG. 11A, taken along the section line shown in FIG. 11B.
Figure 11D:
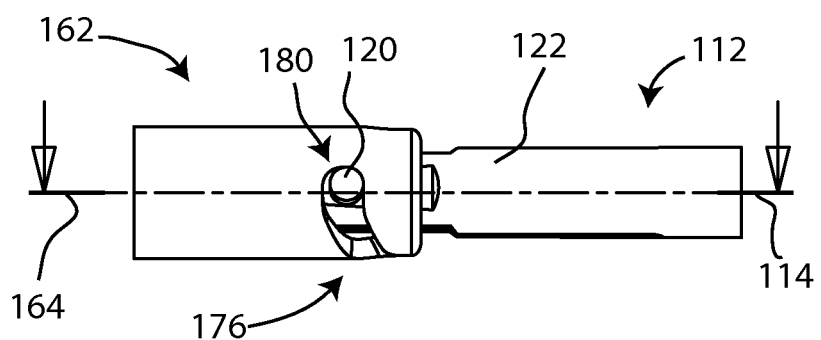
FIG. 11D is a top view of the shaft and socket of FIG. 11A.
Figure 11E:
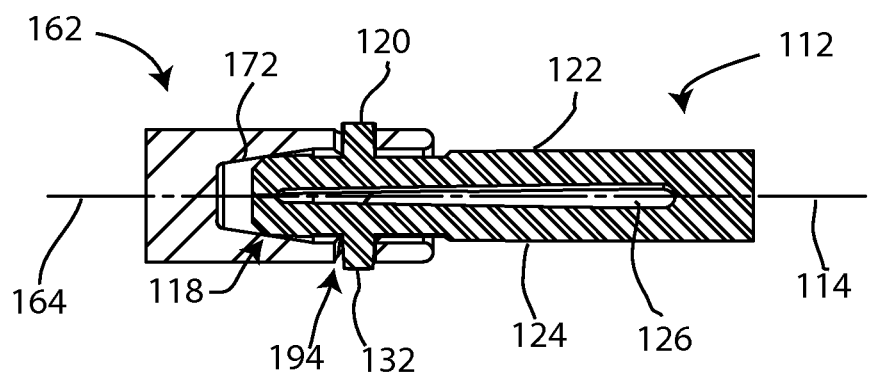
FIG. 11E is a cross sectional view of the shaft and socket of FIG. 11A, taken along the section line shown in FIG. 11D.

In the locked position of FIGS. 11A-E, the axes 114, 164 are substantially aligned, the tip end 118 is wedged in the tapered region 172 so as to at least partially pinch the slit 126 closed, and the first pin 120 is in the terminal end 180, or terminus, of the first slot 176. Thus, the cantilever bodies 122, 124 are at least partially compressed together. The flattened portions 134, 136, 138, 140 provide relief across the incompressible width of the cantilever bodies 122, 124 so that there is clearance with the tapered region 172. In the embodiment of FIGS. 9-11, the second pin 132 is also in a terminal end of the second slot 194. FIGS. 11C and 11E show mutually perpendicular cross sections through the shaft 112 and socket 162 in the locked position. It can be appreciated that tip end 118 of shaft 112 is wedged within tapered region 172 of socket 162, slit 126 is pinched at least partially closed, and flattened portions 134, 136, 138, 140 provide clearance across the width of cantilever bodies 122, 124.

The shaft 112 is selectively movable between the unlocked and locked positions by rotating the shaft 112 within the socket 162. Clockwise rotation of the shaft 112 in the socket 162 moves the shaft 112 from the unlocked position of FIGS. 9A-E to the locked position of FIGS. 11A-E. Counterclockwise rotation of the shaft 112 in the socket 162 moves the shaft 112 from the locked position of FIGS. 11A-E to the unlocked position of FIGS. 9A-E.

The shaft 112 may be selectively movable, relative to the socket 162, to an intermediate position, illustrated in FIGS. 10A-E, in which the tip end 118 makes incipient contact with the tapered region 172, the slit 126 is uncompressed, the cantilever bodies 122, 124 are undeflected, and the first pin 120 is in the first slot 176 between the starting and terminal ends 178, 180. In the embodiment of FIGS. 9-11, the second pin 132 is also in a similar location in the second slot 194. FIGS. 10C and 10E show mutually perpendicular cross sections through the shaft 112 and socket 162 in the intermediate position. It can be appreciated that tip end 118 of shaft 112 has made incipient contact with tapered region 172 of socket 162.

While the present disclosure has been made in the context of a spinal system comprising a trial implant and an inserter tool, the corresponding connection features described herein have a broad range of applications. By way of non-limiting example, the connection features may be applied to surgical trials, rasps, handles, pilot cutters, awls, and mallets, and further applications may be contemplated outside the medical field.

It should be understood that the present components, systems, kits, apparatuses, and methods are not intended to be limited to the particular forms disclosed. Rather, they are intended to include all modifications, equivalents, and alternatives falling within the scope of the claims. They are further intended to include embodiments which may be formed by combining features from the disclosed embodiments.

The claims are not to be interpreted as including means-plus- or step-plus-function limitations, unless such a limitation is explicitly recited in a given claim using the phrase(s) "means for" or "step for," respectively.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

The invention claimed is:

1. A system, comprising:
a shaft, the shaft comprising:
a first center axis, wherein the shaft extends along the first center axis,
a tip end,
a first pin that protrudes from the shaft proximate the tip end, wherein the first pin is generally orthogonal to the first center axis, and
a slit that extends through the tip end and a portion of the shaft, wherein the slit is generally orthogonal to the first pin; and
a socket, the socket comprising:
a second center axis, wherein the socket extends along the second center axis,
an inner diameter,
an open end,
a second end opposite the open end, wherein at least one dimension of the second end is smaller than the inner diameter,
a tapered region between the inner diameter and the second end, and
a first slot that projects into a side wall of the socket, wherein the first slot comprises a starting end at the open end and a terminal end axially spaced apart from the open end, wherein the terminal end is rotationally offset around the side wall from the starting end;
wherein the shaft is selectively movable, relative to the socket, between:
an unlocked position in which the tip end is in the inner diameter, the slit is unpinched, and the first pin is in the starting end; and
a locked position in which the tip end is wedged in the tapered region so as to at least partially pinch the slit, and the first pin is in the terminal end,
wherein the shaft is selectively movable between the unlocked and locked positions by rotating the shaft within the socket so that the first pin slides along the first slot between the starting and terminal ends,
wherein the shaft is fabricated from a material comprising an elastic limit,
wherein, when the tip end is wedged in the tapered region so as to pinch the slit completely closed at the tip end, stresses in the shaft are less than the elastic limit.

2. The system of claim 1, wherein the shaft is selectively movable, relative to the socket, to an intermediate position in which the tip end makes incipient contact with the tapered region, the slit is unpinched, and the first pin is in the first slot between the starting and terminal ends,
wherein, as the shaft moves from the intermediate position to the locked position, a frictional locking force builds between the shaft and the socket to bind the shaft and socket together, and, as the shaft moves from the locked position to the intermediate position, the frictional locking force diminishes.

3. The system of claim 1, wherein the socket comprises a second slot like the first slot, wherein the second slot is rotated around the second center axis relative to the first slot.

4. The system of claim 3, wherein the shaft comprises a second pin like the first pin, wherein the second pin is rotationally positioned around the first center axis relative to the first pin, wherein the shaft is selectively movable, relative to the socket, between:
an unlocked position in which the tip end is in the inner diameter, and the first and second pins are in starting ends of the first and second slots, respectively; and
a locked position in which the tip end is wedged in the tapered region so as to at least partially pinch the slit, and the first and second pins are in terminal ends of the first and second slots, respectively.

5. The system of claim 1, wherein the shaft further comprises:
an outer diameter;
flattened portions along the outer diameter where the slit extends through the shaft; and
a flattened region around the first pin,
wherein the tip end is circumferentially beveled.

6. The system of claim 1, wherein the first slot comprises:
a starting portion that extends parallel to the second center axis;
a terminal portion that extends substantially perpendicular to the second center axis; and
a helical portion between the starting and terminal ends.

7. The system of claim 1, wherein a portion of the first slot is spaced farther apart from the open end than is the terminal end.

8. The system of claim 1, wherein the terminal end is rotationally offset ninety degrees around the side wall from the starting end.

9. A system, comprising:
a shaft, the shaft comprising:
a first longitudinal axis, wherein the shaft extends along the first longitudinal axis,
an outer diameter, and
a tip end, wherein the tip end is split to comprise a plurality of cantilever bodies, wherein one of the cantilever bodies comprises a first tab, wherein the first tab protrudes outwardly beyond the outer diameter; and
a socket, the socket comprising:
a second longitudinal axis, wherein the socket extends along the second longitudinal axis,
an inner diameter,
an open end,
a second end opposite the open end, wherein at least one dimension of the second end is smaller than the inner diameter,
a tapered region inside the socket between the inner diameter and the second end, and
a first slot in a side wall of the socket, wherein the first slot comprises a mouth at the open end and a terminus axially spaced apart from the open end, wherein the terminus is angularly offset around the side wall from the mouth;
wherein the shaft is selectively movable, relative to the socket, between:
an unlocked position in which the tip end is in the inner diameter, the cantilever bodies are uncompressed, and the first tab is in the mouth; and
a locked position in which the tip end is wedged in the tapered region so as to at least partially compress the cantilever bodies together, and the first tab is in the terminus,
wherein the shaft is selectively movable between the unlocked and locked positions by rotating the shaft within the socket so that the first tab slides along the first slot between the mouth and terminus,
wherein the shaft is fabricated from a material comprising an elastic limit, wherein, when the tip end is wedged in the tapered region so that the cantilever bodies touch together at the tip end, stresses in the shaft are less than the elastic limit.

10. The system of claim 9, wherein the shaft is selectively movable, relative to the socket, to an intermediate position in which the tip end makes incipient contact with the tapered region, the cantilever bodies are uncompressed, and the first tab is in the first slot between the mouth and terminus,
wherein, as the shaft moves from the intermediate position to the locked position, a frictional locking force develops between the shaft and the socket to bind the shaft and socket together, and, as the shaft moves from the locked position to the intermediate position, the frictional locking force wanes so that the shaft and socket are mutually separable.

11. The system of claim 9, wherein the socket comprises a second slot like the first slot, wherein the second slot is rotated around the second longitudinal axis from the first slot,
wherein the shaft comprises a second tab like the first tab, wherein the second tab is rotated around the first longitudinal axis from the first tab,
wherein, when the shaft and the socket are operatively assembled, the first tab engages the first slot and the second tab engages the second slot.

12. The system of claim 9, wherein the tip end is circumferentially beveled.

13. The system of claim 9, wherein the first slot comprises:
a starting portion that extends parallel to the second longitudinal axis;
a terminal portion that extends substantially perpendicular to the second longitudinal axis; and
a helical portion between the mouth and terminus.

14. The system of claim 9, wherein a portion of the first slot is spaced farther apart from the open end than is the terminus.

15. The system of claim 9, wherein the terminus is angularly offset ninety degrees around the side wall from the mouth.

16. A locking mechanism, comprising:
a shaft comprising an outer diameter and a working end, wherein the working end is circumferentially beveled, wherein the working end is split to comprise a plurality of resilient prongs, wherein each one of the prongs carries a tab, wherein each one of the tabs projects outwardly from the outer diameter; and
a socket comprising an inner diameter, an open end, and a longitudinal axis, wherein the socket extends along the longitudinal axis, wherein the open end comprises a plurality of grooves in the inner diameter, wherein each one of the grooves follows a path between a starting point and a terminal point, wherein the terminal point is offset from the starting point along the longitudinal axis and around the inner diameter, wherein the socket further comprises a tapered constriction distant from the open end;
wherein the shaft is selectively movable, relative to the socket, between:
an unlocked position in which the working end is in the inner diameter, the prongs are undeflected, and the tabs are in the grooves proximate the starting points; and
a locked position in which the working end is wedged in the tapered constriction so as to at least partially deflect the prongs, and the tabs are in the grooves proximate the terminal points,
wherein the shaft is selectively movable between the unlocked and locked positions by rotating the shaft within the socket so that the tabs slide along the grooves between the starting and terminal points,
wherein the shaft is fabricated from a material comprising an elastic limit,
wherein, when the working end is wedged in the tapered region so as to cause the prongs to touch together at the working end, stresses in the shaft are less than the elastic limit.

17. The locking mechanism of claim 16, wherein the plurality of tabs and the plurality of grooves are arranged in complementary circular arrays.

18. The locking mechanism of claim 16, wherein the shaft is selectively movable, relative to the socket, to an intermediate position in which the working end makes incipient contact with the tapered constriction, the prongs are undeflected, and the tabs are in the grooves between the starting and terminal points,
wherein, as the shaft moves from the intermediate position to the locked position, a frictional locking force develops between the shaft and the socket to bind the shaft and socket together, and, as the shaft moves from the locked position to the intermediate position, the frictional locking force wanes.

19. The locking mechanism of claim 16, wherein each one of the grooves comprises:
a starting portion that extends parallel to the longitudinal axis;

a terminal portion that extends substantially perpendicular to the longitudinal axis; and a helical portion between the starting and terminal points.

20. The locking mechanism of claim 16, wherein the terminal point is offset ninety degrees around the inner diameter from the starting point.

* * * * *